US005486693A

United States Patent [19]
Achter et al.

[11] Patent Number: 5,486,693
[45] Date of Patent: Jan. 23, 1996

[54] DETECTION OF TURBID CONTAMINANTS IN CONTAINERS BY DETECTING SCATTERED RADIANT ENERGY

[75] Inventors: Eugene K. Achter, Lexington; Helmut W. Klotzsch, Groton; Craig D. Thompson, Natick; Fuquan Gao, Cambridge; Jonathan E. Bosworth, Acton, all of Mass.

[73] Assignee: Thermedics Detection Inc., Chelmsford, Mass.

[21] Appl. No.: 337,817

[22] Filed: Nov. 8, 1994

Related U.S. Application Data

[63] Continuation-in-part of Ser. No. 268,198, Jun. 29, 1994, which is a continuation-in-part of Ser. No. 198,217, Feb. 17, 1994.

[51] Int. Cl.⁶ .................................................... G01N 21/24
[52] U.S. Cl. ................ 250/223 B; 250/226; 250/339.06; 356/240
[58] Field of Search ............................ 250/223 B, 226, 250/339.06–339.09; 356/239, 240, 409; 209/523, 524; 382/31, 43

[56] References Cited

U.S. PATENT DOCUMENTS

| | | | |
|---|---|---|---|
| 4,221,961 | 9/1980 | Peyton | 250/223 B |
| 4,459,023 | 7/1984 | Reich et al. | 356/240 |
| 4,490,042 | 12/1984 | Wyatt | 356/340 |
| 4,551,627 | 11/1985 | Reich | 250/223 B |
| 4,830,192 | 5/1989 | Plester et al. | 209/523 |
| 4,858,768 | 8/1989 | Plester | 209/523 |
| 4,998,824 | 3/1991 | Littlejohn et al. | 250/226 |
| 5,002,397 | 3/1991 | Ingrum et al. | 250/226 |
| 5,067,616 | 11/1991 | Plester et al. | 209/523 |
| 5,086,483 | 2/1992 | Capps | 382/31 |
| 5,150,307 | 9/1992 | McCourt et al. | 250/223 R |

*Primary Examiner*—Stephone B. Allen
*Attorney, Agent, or Firm*—Fish & Richardson

[57] ABSTRACT

To detect a turbid contaminant in a moving container, radiant energy having a wavelength that is absorbed by contents of the moving container that include the turbid contaminant at a different level than energy having the wavelength is absorbed by contents of the moving container that include a non-contaminant is directed into the container. Thereafter, a level of radiant energy scattered by contents of the container is detected. The presence of a turbid contaminant is indicated when the detected level of scattered radiant energy differs from a threshold level.

33 Claims, 11 Drawing Sheets

DETECTION OF TURBID CONTAMINANTS IN CONTAINERS BY DETECTING SCATTERED RADIANT ENERGY

CROSS-REFERENCE TO RELATED APPLICATIONS

This application is a continuation-in-part of U.S. patent application Ser. No. 08/268,198, entitled "DETECTION OF TURBID OR FOAMING CONTAMINANTS IN CONTAINERS", which was filed on Jun. 29, 1994, and is itself a continuation-in-part of U.S. patent application Ser. No. 08/198,217, which is entitled "SPECTRAL DETECTION OF CONTAMINANTS IN CONTAINERS" and was filed on Feb. 17, 1994. The disclosure of each of these applications is hereby incorporated by reference.

BACKGROUND OF THE INVENTION

The invention relates to detection of contaminants in containers, particularly contaminants whose presence is manifested by turbidity of a liquid.

The popularity of refillable containers has increased as the costs, both social and financial, associated with disposal of packaging have become less acceptable. For example, in many countries, water and other beverages are sold in refillable bottles. These bottles are often made from a type of plastic known as polyethylene terephthalate.

After use, refillable containers are returned to a bottling plant where they are cleaned and inspected before being refilled. This inspection, in addition to checking for physical damage such as cracks, screens the containers to eliminate those that include contaminants that might degrade the flavor, safety, or other qualities of the product that they contain. The risk of contamination is greater when a container is made from plastic, as opposed to glass, because some contaminants can be absorbed into the plastic walls of the container. Absorbed contaminants can persist despite cleaning procedures, and can later leach into the product.

As used herein, "contaminant" means any substance that can be detected in a container by the detection system of the invention and whose presence is incompatible with the product with which the container is to be filled. For example, detergents are contaminants with respect to beverage containers, and flavored beverages may be contaminants with respect to bottled water.

As also used herein, "turbid contaminant" means a contaminant the presence of which in or with a liquid results in the liquid and contaminant mixture being turbid or unclear so as to scatter radiant energy directed into the liquid and contaminant mixture. Where the context so indicates, the definition of "liquid" includes a liquid and contaminant mixture.

Though some contaminants, such as detergents and fabric softeners, are visibly colored and can be detected by human inspectors, such human visual inspection is undesirable when bottles or other containers are moving on high speed conveyors and stopping or touching the bottles to perform an inspection is undesirable or overly expensive. Moreover, such human visual inspection is subject to lapses in attention by the inspectors.

SUMMARY OF THE INVENTION

The invention features detection of turbid contaminants in a moving container, such as a bottle moving along a conveyor line, by directing radiant energy into the container and measuring a level of radiant energy scattered by the contents of the container. For example, radiant energy may be directed into an opening at the top of the container so that the radiant energy encounters liquid in the bottom of the container. If the liquid in the container is turbid, a high level of radiant energy will be scattered by the liquid.

According to the invention, the scattered radiant energy encounters an appropriately positioned detector so that contaminants such as detergents are detected by monitoring the level of energy incident on the detector and indicating the presence of a contaminant when this level differs from a threshold level. When contaminants are detected, the container is rejected.

The radiant energy may include energy having a wavelength that is absorbed at a different level by contents of the container that include non-contaminants than energy having the wavelength is absorbed by contents of the container that include contaminants. For example, when the container is a plastic bottle for cola-flavored beverages, the radiant energy may include energy having a wavelength (e.g., a "green" wavelength such as 543 nanometers) that is absorbed to a higher degree by non-contaminants such as residues of the cola-flavored beverages than it is absorbed by contaminants such as white detergent. This permits a bottle containing the acceptable beverage residue to be distinguished from a bottle containing the unacceptable detergent even when, due to the presence of harmless mold in the beverage residue, the beverage residue is turbid. Though both a turbid cola-flavored beverage residue and a white detergent would scatter the radiant energy of the green wavelength, the cola-flavored beverage residue would absorb more of the incident and scattered energy than would the detergent, and less scattered energy would be detected from the beverage residue than would be detected from the detergent. Thus, the presence of a turbid contaminant would be indicated when the detected level of scattered radiant energy exceeds a threshold level.

In most cases, use of radiant energy of a single wavelength (e.g., 543 nanometers) which yields a different amount of scattered energy after interacting with contaminated liquid than with uncontaminated liquid is sufficient to distinguish between the turbid cola-flavored beverage residue and the detergent in most cases. However, in some cases, a turbid cola-flavored beverage residue may actually produce more scattered energy of this single wavelength than would a detergent. For example, a diluted detergent may scatter an amount of energy that is comparable to or less than an amount of energy scattered by a turbid cola-flavored beverage residue but not absorbed by the residue, and the energy that is detected from a bottle containing turbid cola-flavored beverage residue may exceed the energy detected from a bottle containing a diluted detergent.

Because it is desirable in many cases to detect even diluted contaminants, the threshold level may be further adjusted by monitoring the energy scattered by each container in a set of contaminated containers and setting the threshold level to a value that would not accept the contaminated containers. As indicated above, this adjusted level may be so low that some uncontaminated containers, such as those containing turbid beverage residues, may be rejected.

To limit the number of uncontaminated containers that are rejected, multiple-wavelength radiant energy may be employed to distinguish between turbid beverage residues and diluted detergents. For example, radiant energy having a first wavelength (e.g., the "green" wavelength) that cola-flavored beverages strongly absorb and a second wavelength (e.g., a "red" wavelength such as 632 nanometers) that cola-flavored beverages absorb to a lesser degree than they absorb energy having the first wavelength may be used. In such an approach, when a detected level of radiant energy exceeds an empirically determined threshold level associated with one or both of the two wavelengths, a turbid cola-flavored beverage residue would be distinguished from a diluted detergent by comparing the levels of scattered energy of the first and second wavelengths or generating a value (e.g., a ratio) that is a function of both levels.

A turbid cola-flavored beverage residue would absorb more of the first wavelength energy than it would of the second wavelength energy. Thus, scattered radiant energy of the first wavelength would be detected to a lesser degree than would scattered radiant energy of the second wavelength when a turbid cola-flavored beverage was present.

By contrast, a diluted detergent would scatter similar levels of energy of both the first and second wavelengths. (Because, in general, scattered intensity is inversely proportional to the fourth power of the wavelength, a white detergent may actually yield slightly more scattered energy of the first wavelength than energy of the second wavelength.) Thus, a system that used radiant energy of both the first and second wavelengths could distinguish between a turbid cola-flavored beverage residue and a diluted detergent in a bottle by generating a ratio of the levels of energy of each wavelength that are scattered by the contents of the bottle and comparing the ratio to a threshold level. The threshold level is determined empirically by monitoring the ratios produced by a set of uncontaminated bottles and setting the threshold level to a value that would not result in the uncontaminated bottles being rejected and that is close to the ratios produced by the uncontaminated bottles. For example, when a detected ratio in excess of the threshold level indicates the presence of a contaminant, the threshold level would be set to the smallest value that would not reject the uncontaminated bottles. A set of contaminated bottles could also be monitored and the results from both tests could be used in setting the threshold level.

In one aspect, generally, the invention features detecting contaminants in a moving container, such as a bottle moving on a conveyor line, by directing into the container radiant energy having a wavelength that is absorbed by contents of the container that include a contaminant at a different level than energy having the wavelength would be absorbed by contents of the container that include a non-contaminant, detecting a level of radiant energy scattered by contents of the container, and indicating the presence of a contaminant when the detected level of scattered radiant energy bears a predetermined relationship to a threshold level.

When energy having the selected wavelength is absorbed by the contents of the container that include the non-contaminant to a greater degree than the energy is absorbed by contents of the container that include the contaminant, the presence of a contaminant is indicated when the detected level of scattered radiant energy exceeds a threshold level. For example, When the contents of the container include residue of a cola-flavored beverage and the cola-flavored beverage residue comprises a non-contaminant, the wavelength is selected so that energy having the wavelength is substantially absorbed by the cola-flavored beverage residue and the presence of a contaminant is indicated when the detected level of scattered radiant energy exceeds a threshold level.

In a preferred approach, energy scattered in a different direction than that at which the radiant energy is directed into the container is measured and, provided that higher levels of scattered energy are associated with contaminants, the presence of a contaminant is indicated when the energy incident on the detector exceeds a threshold. To reduce the effects of background energy, the radiant energy may be modulated before it is directed into the moving container and demodulated after detection.

The radiant energy may also include a second wavelength. In this case, the level at which energy having the second wavelength is scattered is determined. If this level exceeds a threshold, the relative levels at which energy having the first and second wavelengths are scattered is determined, and the presence of a contaminant is indicated when the first and second levels of scattered radiant differ in a way that indicates that a contaminant is present. For example, when energy having the first wavelength is substantially absorbed by a non-contaminant and energy having the second wavelength is substantially transmitted by the non-contaminant, the presence of a contaminant is indicated when (1) the energy having the second wavelength is scattered to an extent that exceeds a threshold level and (2) energy having the first wavelength is scattered similarly to energy having the second wavelength or when a comparison of their scattered energy levels satisfies a predetermined criterion. The levels of scattered radiant energy may be compared by producing a ratio of their values.

To detect contaminants in a moving container, liquid is added to the container to ensure the presence of a minimal amount needed for proper detection.

The invention also features examining the color, or spectral characteristics, of the container and any contents thereof and, based on this examination, either adjusting the threshold for detection of scattered energy, spectrally detecting contaminants, or both. Spectral characteristics of liquid in the container are determined by subjecting the container and the liquid to wideband radiant energy and obtaining a resulting spectrum. This spectrum, without consideration of the intensity of the radiant energy directed at the container, is then compared against a library of stored reference spectra to determine whether contaminants are present. If contaminants are determined to be present, the container is rejected. The results of the comparison can also be used to adjust the thresholds for turbid contaminant detection. In general, the radiant energy used to detect turbid contaminants is concentrated in one or more narrow wavelength bands while the radiant energy used to generate frequency spectra covers a much wider band of wavelengths.

The invention is particularly useful for detecting contaminants in clear plastic bottles, such as those made from polyethylene terephthalate. However, the invention is also useful in detecting contaminants within other types of containers, containers made from other materials, and tinted containers. Generally, the only limitation on suitable containers is that they be made from materials that are translucent to the radiant energy being employed.

In a preferred embodiment, the invention features a turbid contaminant detection system that includes a radiant energy source for directing radiant energy having a wavelength that is absorbed by contents of a moving container that include a contaminant at a different level than energy having the wavelength is absorbed by a contents of the moving container than include a non-contaminant, the radiant energy source being positioned to direct the radiant energy into the moving container. The system also includes a detector for detecting radiant energy scattered by contents of the moving container, and a processor for monitoring the detected radiant energy and indicating the presence of a contaminant when the level of detected radiant energy differs from a threshold level.

The detector may be positioned near the bottom of the moving container to detect light scattered by turbid liquid within the container.

The radiant energy source may include a first laser source for producing a first laser beam having energy of a first wavelength and a second laser source for producing a second laser beam having energy of a second wavelength. Typically, the radiant energy source also includes a dichroic reflector that combines the first and second laser beams into a single beam, and an adjustable positioning mirror that directs the beam into the container.

The system may also include an illuminator for directing radiant energy having a wide range of frequencies at the moving container so that the radiant energy is modified by contents of the moving container to produce modified radiant energy, and a second detector for detecting a portion of the modified radiant energy so that the processor can obtain spectral information related to the contents of the container. The processor may use the spectral information to modify the threshold level used for turbid contaminant detection, or may compare the spectral information with a library of reference spectra and indicate the presence or absence of a contaminant based on the relationship between the spectral information and the reference spectra, or may do both. This system, which is preferably entirely automated, works effectively even when containers are moving past the system at rates on the order of 400 containers per minute or greater.

To ensure that spectral information is obtained from the detector at proper times, the system can include first, second and third position sensors that signal the processor when a container is in, respectively, a first, second or third position. The processor responds to the signal from the first position sensor by obtaining first position spectral information from the detector, to the signal from the second position sensor by obtaining second position spectral information from the detector, and to the signal from the third position sensor by measuring scattered radiant energy. The processor then compares the first and second position spectral information against the library of reference spectra, and compares the scattered energy information from measurements at the third position against a threshold, to determine whether a contaminant is present.

The contaminant detection system preferably is positioned downstream of a liquid supplier that adds a quantity of liquid to the container before the container arrives at the illuminator. To minimize the amount of liquid required, the illuminator, radiant energy source, and detectors are positioned so that radiant energy from the illuminator and the radiant energy source reaches the detectors after passing through and interacting with a region substantially near the bottom of the container. Typically this region is within one inch, and often within one quarter of an inch, of the bottom of the container.

Other features and advantages of the invention will be apparent from the following description of preferred embodiments, and from the claims.

DESCRIPTION OF PREFERRED EMBODIMENTS

Figure 1:
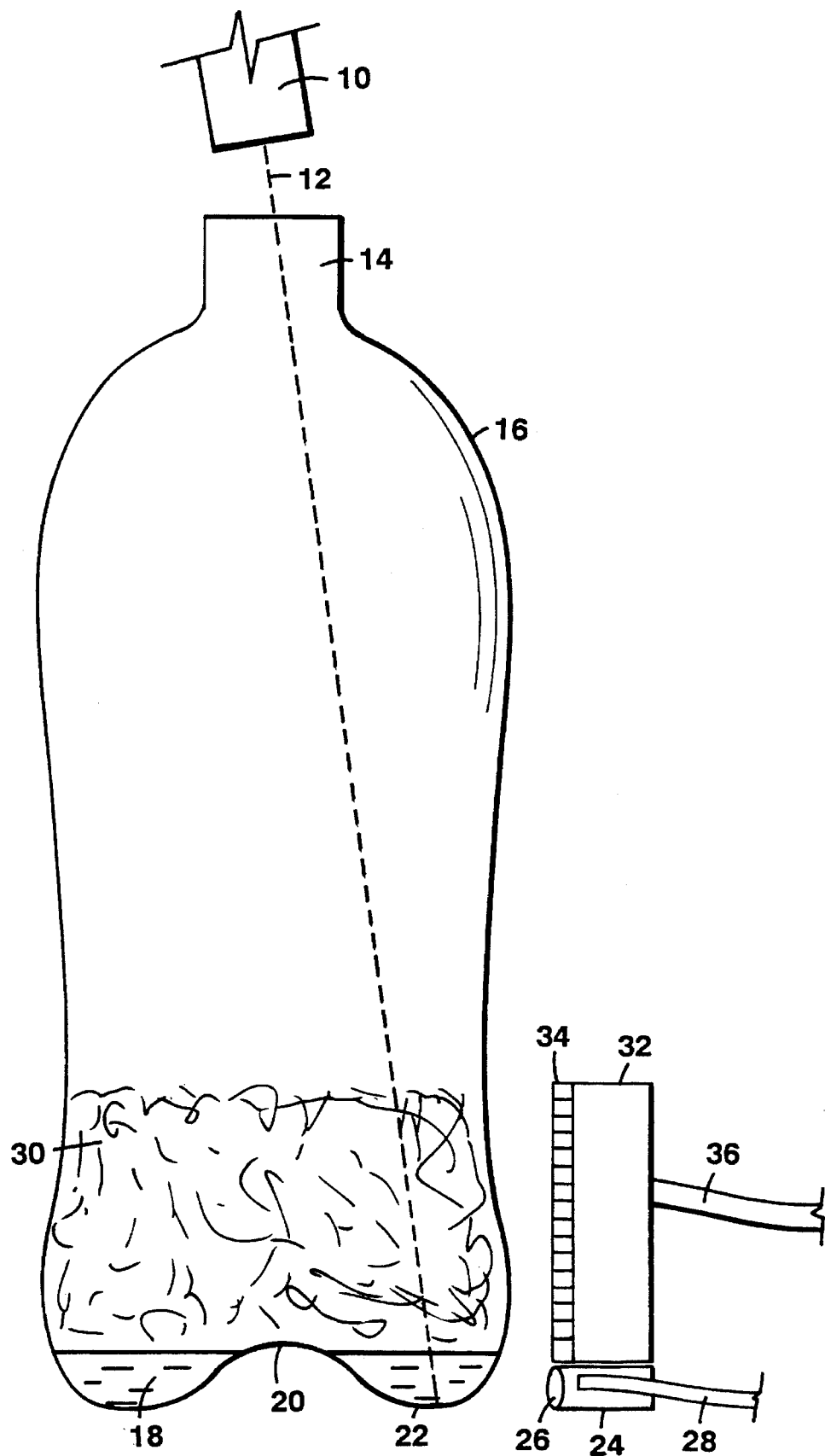
FIG. 1 is a side view of a bottle and a portion of a turbid contaminant and foam detection system.

With reference to FIG. 1, a radiant energy source 10 is positioned to direct a radiant energy beam 12 into the open neck 14 of a bottle 16 and into an annular ring of liquid 18 that is formed by a convex bulge 20 in the center of the base 22 of the bottle. When the liquid is turbid (e.g., due to the presence of a turbid contaminant) and the radiant energy is in the visible portion of the spectrum, light scattered by particles in the liquid causes the radiant energy beam to appear visually as a column of light in the liquid. A turbid contaminant detector 24 detects this column of light by monitoring the radiant energy scattered by the liquid. The turbid contaminant detector is positioned adjacent to the outer wall of the bottle near its base, and includes a collecting lens 26 and an optical fiber 28. The collecting lens 26 focusses any received radiant energy on the optical fiber 28.

When foam 30, such as would be caused by detergents and similar substances, is present on top of the liquid in the bottle, light scattered by the foam may be detected by a foam detector 32 that includes optical fibers having receiving ends are arranged in a vertical line array 34 adjacent to the bottle. The fibers are gathered into a bundle forming a round array 36 at the opposite ends of the fibers. The foam detector is positioned next to the bottle with the vertical line array of fibers extending from about one quarter to two inches from the bottom of the bottle. The round array end 36 of the fibers is positioned adjacent to a photodetector 38 (see FIG. 4) so that radiant energy transmitted by the fibers is incident on the photodetector 38. Thus, when foam is present, light scattered by the foam strikes one or more fibers of the vertical line array 34, and is directed to the photodetector 38.

When radiant energy incident on photodetector 38 exceeds a threshold amount, this indicates that foam is present.

Figure 2:
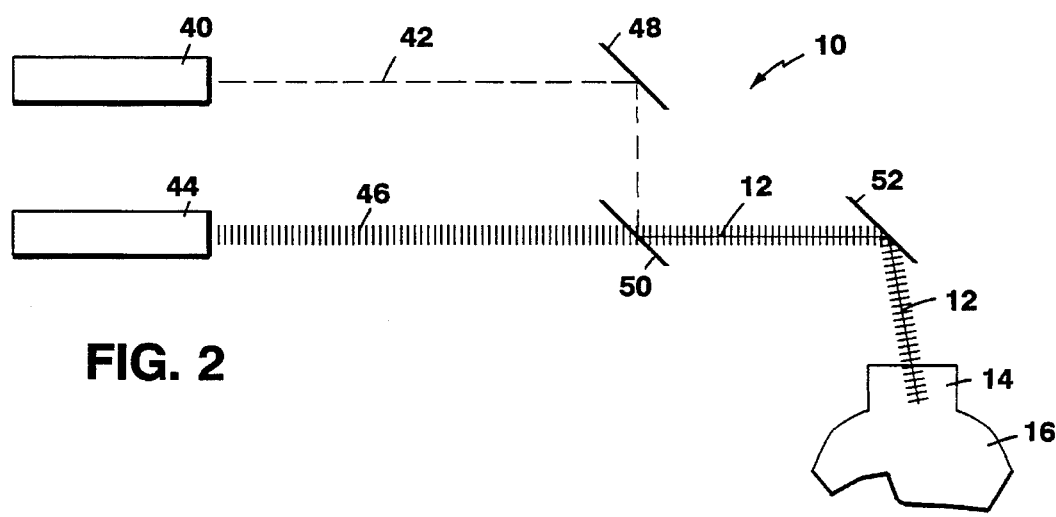
FIG. 2 is a schematic diagram of a radiant energy source of the turbid contaminant and foam detection system of FIG. 1.

Radiant energy source 10 may be configured to produce a multiple-wavelength radiant energy beam where, as used herein, "multiple-wavelength" refers to energy concentrated in two or more discrete wavelengths or in narrow wavelength bands such as the bands from 665 to 675 nanometers and from 538 to 548 nanometers. For example, with reference to FIG. 2, radiant energy source 10 may include a first laser source 40 that produces a laser beam 42 having energy of a first wavelength, and a second laser source 44 that produces a laser beam 46 having energy of a second wavelength. Laser beam 42 may be a green beam with a wavelength of 543 nanometers while laser beam 46 is a red beam with a wavelength of 632 nanometers. Laser sources 40 and 44 may be implemented using helium/neon continuous wave gas lasers such as Model Nos. 05LHR111 (red) and 05LGR025 (green) available from Melles Griot of Irvine, Calif. Laser sources 40 and 44 may also be implemented using diode lasers. When only a single wavelength is necessary or desirable, radiant energy source 10 can be implemented using only laser source 40.

When two laser sources are used, laser beams 42 and 46 are combined by a mirror 48 and a dichroic reflector 50. Mirror 48 is positioned in the path of beam 42 and is angled to direct beam 42 in a path that intersects beam 46. Dichroic reflector 50, which reflects beam 42 and transmits beam 46, is positioned at the point where beam 42 intersects beam 46, and is oriented so as to direct beam 42 along a path that is co-linear with beam 46 so that beams 42 and 46 form radiant energy beam 12. Dichroic reflector 50 may be implemented using a red reflective filter such as Model No. CR600 available from Corion Optics of Holliston, Mass.

A positioning mirror 52 directs radiant energy beam 12 into the opening 14 in the top of a bottle 16. Positioning mirror 52 is adjustable to control the path of beam 12 as it enters a bottle 16.

Because beams 42 and 46 are co-linear, radiant energy of each wavelength follows a common path through the liquid 18 in the bottle 16. This ensures that scattered levels of radiant energy of both wavelengths will be obtained from the same volume element of the liquid, and that a comparison of the scattered levels of energy of the two wavelengths will provide meaningful information. If beams 42 and 46 were allowed to travel along separate paths in which beam 42 travelled through a first volume of the liquid and beam 46 travelled through a second volume of the liquid having an unknown relationship to the first volume, a comparison of the scattered level of energy from beam 42 with the scattered level of energy from beam 46 might not provide meaningful information about the relative degree to which the liquid scattered each beam.

To reduce the effects of background radiation, laser sources 40 and 44 may be configured to produce frequency modulated laser beams. For example, laser sources 40 and 44 could be implemented using diode lasers of the appropriate wavelength and modulated at 12 kHz.

In another approach, radiant energy source 10 could be implemented using a broadband source such as a white light. In this case, colored filters or dispersive elements such as prisms or diffraction gratings would be interposed between the light and the bottles, between the bottles and the photodetectors, or both. However, use of one or more discrete wavelengths offers increased energy efficiency and is preferred for that reason.

Figure 3:
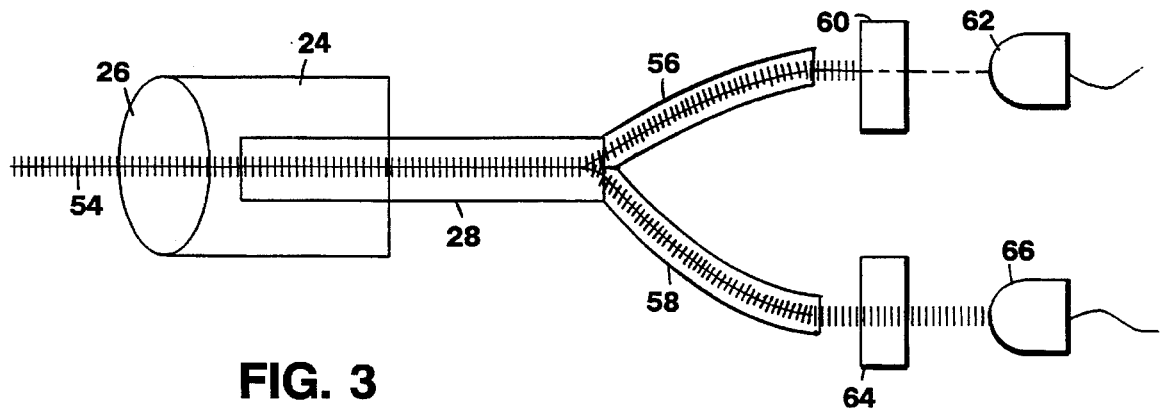
FIG. 3 is a block diagram of a turbid contaminant detector of the turbid contaminant and foam detection system of FIG. 1.
Figure 4:
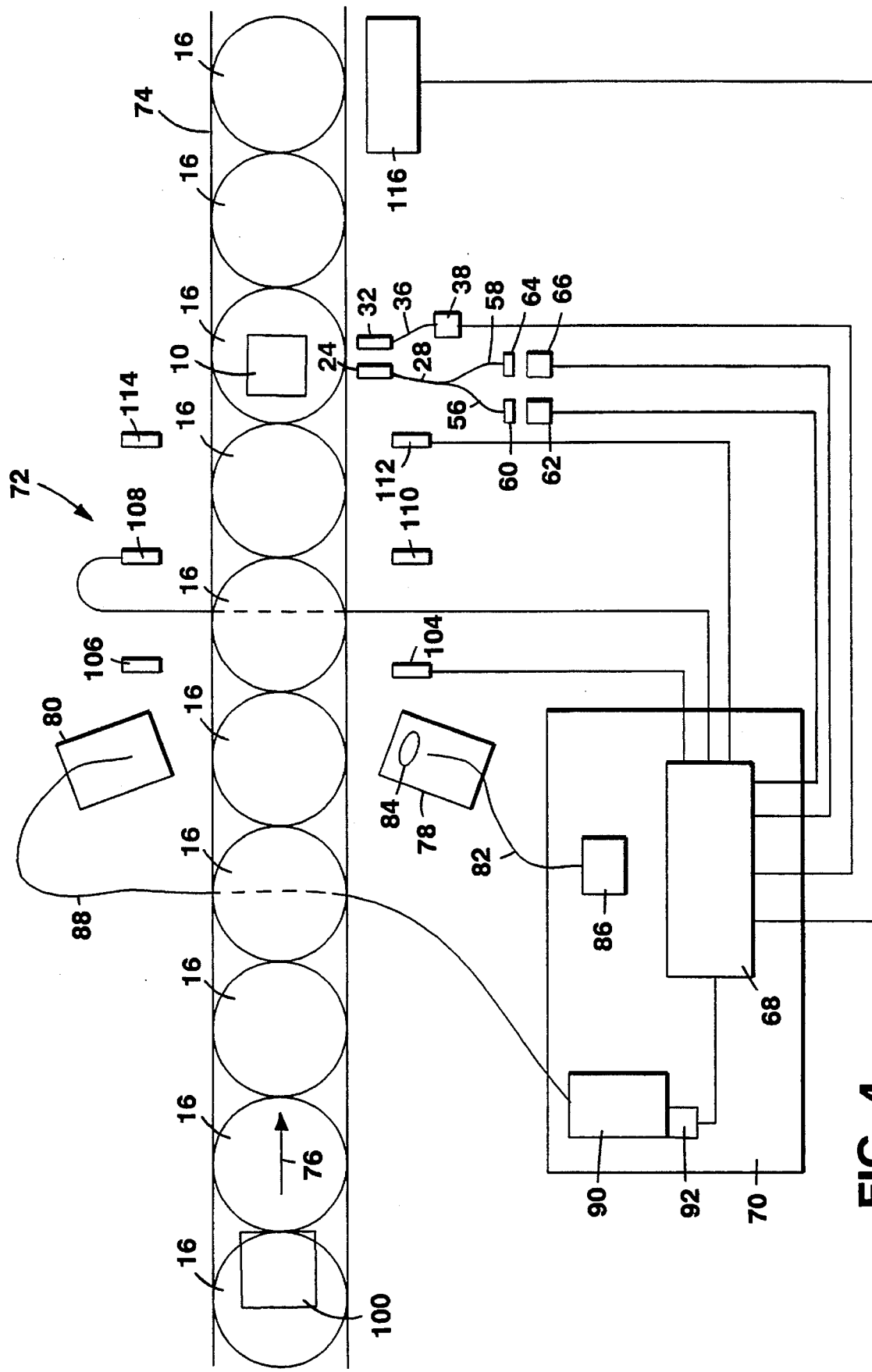
FIG. 4 is a schematic plan view of a portion of a bottle conveyor with a contaminant detection system including the turbid contaminant and foam detection system of FIG. 1.

With reference to FIGS. 3 and 4, multiple-wavelength radiant energy 54 scattered by the liquid and emerging from a bottle 16 is received by a turbid contaminant detector 24. This energy passes through collecting lens 26 and into a first end of optical fiber 28. The second end of optical fiber 28 is split into or connected to optical fibers 56 and 58 so that multiple-wavelength radiant energy travels through each of these fibers.

Optical fiber 56 is positioned so that multiple-wavelength radiant energy exiting optical fiber 56 is directed to a first filter 60 that is configured to pass wavelengths corresponding to laser beam 42 and to block other wavelengths, including those corresponding to laser beam 46. A photodetector 62, such as a photodiode, is positioned to detect radiant energy passing through filter 60. Thus, photodetector 62 detects radiant energy that is scattered by liquid 18 and has a wavelength corresponding to laser beam 42.

Optical fiber 58 is positioned so that multiple-wavelength radiant energy exiting optical fiber 58 is directed to a second filter 64 that is configured to pass wavelengths corresponding to laser beam 46 and to block other wavelengths, including those corresponding to laser beam 42. A photodetector 66, such as a photodiode, is positioned to detect radiant energy passing through filter 64. Thus, photodetector 66 detects radiant energy that is scattered by liquid 18 and has a wavelength corresponding to laser beam 46.

If radiant energy having only a single wavelength were employed, optical fiber 58, filter 64 and photodetector 66 would be eliminated.

As shown in FIG. 4, photodetectors 62, 66 and 38 are connected to a processor 68 that receives and electronically processes signals from the photodetectors 62, 66 and 38 and other sensors as part of a control unit 70. Processor 68 digitizes the signals from photodetectors 62 and 66 and uses these signals to determine whether turbid contaminants are present in a particular bottle 16. If foam detector 32 is in use, processor 68 also digitizes signals from photodetector 38 and uses those signals to determine whether foaming contaminants are present. When laser sources 40 are 44 are configured to produce frequency modulated beams, processor 68 and photodetectors 62, 66 and 38 are configured to detect only frequency modulated energy.

In general, processor 68 determines that a turbid contaminant is present if the signal from photodetector 62 exceeds a threshold level associated with photodetector 62 or the signal from photodetector 66 exceeds a threshold level associated with photodetector 66, and a ratio of the two signals does not indicate that an acceptable material, such as the cola beverage residue discussed above, is present. Prior to determining the ratio of the two signals, processor 68 subtracts a baseline value, if any, from each signal. Thus, when red and green wavelengths are used, the ratio, R, is determined as:

$$R = \frac{\text{green} - \text{baseline}_{green}}{\text{red} - \text{baseline}_{red}}$$

where the baseline value for each signal corresponds to the level of background noise for that signal.

If photodetector 32 is in use, processor 68 determines that a foaming contaminant is present if the signal from photodetector 38 exceeds a threshold level associated with photodetector 38.

The thresholds associated with each photodetector, as well as the threshold associated with the ratio, are determined empirically and can vary based on, for example, ambient lighting conditions, the level of radiant energy directed into the bottle (i.e. the power of the radiant energy source that produces the radiant energy directed into the bottle), the geometry and composition of the bottle, and the position of a detector that detects the scattered radiant energy. Generally, the energy levels scattered by a set of uncontaminated bottles are monitored. Thereafter, the thresholds are set to values that do not reject the uncontaminated bottles and are close to the levels of radiant energy detected from the uncontaminated bottles. For example, when the presence of a contaminant is indicated by a level of detected radiant energy that exceeds the threshold level, the threshold level would be set to the lowest level that would not reject the uncontaminated bottles. A set of contaminated bottles may also be monitored and the threshold may be adjusted so that the contaminated bottles are rejected.

In a particular application using both "green" and "red" wavelengths, processor 68 determines whether a contaminant is present by monitoring the signal from photodetector 66. If this signal indicates that a turbid liquid is present (i.e., if the detected scattered energy having the "red" wavelength exceeds a threshold level), then processor 68 generates the ratio as noted above and examines the ratio to determine whether the turbid liquid is actually a turbid contaminant. Though comparable results could be achieved by monitoring the signal from photodetector 62, the signal from photodetector 66 is monitored because it provides convenience of calculation by ensuring that processor 68 will not encounter a division-by-zero error when generating the ratio.

Similarly, in a particular application using only the "green" wavelength, processor 68 determines whether a contaminant is present by monitoring the signal from photodetector 62. If this signal indicates that a turbid liquid is present (i.e., if the detected scattered energy having the "green" wavelength exceeds a threshold level), then processor 68 indicates that a contaminant is present. The processor 68 then sends a signal to the rejector 116 (FIG. 4) which responds by removing the bottle 16 from the conveyor 74.

With further reference to FIG. 4, turbid contaminant detector 24 and foam detector 32 are typically employed in conjunction with a spectral contaminant detection system 72 that is positioned to detect contaminants in containers, such as bottles 16, by analyzing spectral characteristics of liquids contained in the bottles as the bottles move along a conveyor 74 in the direction indicated by arrow 76. Because contaminants may be present as liquids in the bottles or may leach or desorb from walls of the bottles into liquids contained therein, the spectral characteristics of the liquids indicate the presence of such contaminants. Thus, by comparing the spectral characteristics of a bottle and the liquid contained therein to characteristics of bottles containing contaminated or uncontaminated liquids, the spectral contaminant detection system determines whether contaminants are present in the bottle.

System 72 includes a radiant energy source or illuminator 78 and a detector 80. The illuminator is positioned to direct radiant energy at a bottle so that the radiant energy encounters liquid contained in the bottle. The detector is positioned to detect radiant energy from the illuminator after that radiant energy has encountered the liquid contained in the bottle.

The illuminator includes a fiber optic bundle 82 coupled to a lens 84. The fiber optic bundle transmits radiant energy from a lamp 86 located in control unit 70 to the lens 84, which focusses the radiant energy and directs the focussed radiant energy toward a bottle 16. The lamp is typically a halogen lamp, but other sources of radiant energy such as, for example, a xenon flashtube that is controlled to strobe at appropriate times, could be used.

The detector 80 includes a fiber optic bundle 88 that receives some of the radiant energy from lens 84 after it has encountered liquid in the bottle. Fiber optic bundle 88 transmits the radiant energy to an optical spectrometer 90 in the control unit 70. Within the optical spectrometer, a series of mirrors focusses the transmitted radiant energy on a diffraction grating that separates the transmitted radiant energy into wavelength components and directs each wavelength component to a different pixel of a linear detection array 92. Typically, linear detection array 92 is implemented as a diode array or a charge coupled device ("CCD") having about two hundred fifty (e.g., 256) pixels or about one thousand (e.g., 1024) pixels.

Use of fiber optic bundles 82 and 88, which may be two meters or greater in length, allows the control unit 70 to be positioned a substantial distance away from the conveyor and the bottles, and thereby minimizes the exposure of the control unit to the potentially wet or otherwise hostile environment at the conveyor.

Figure 6:
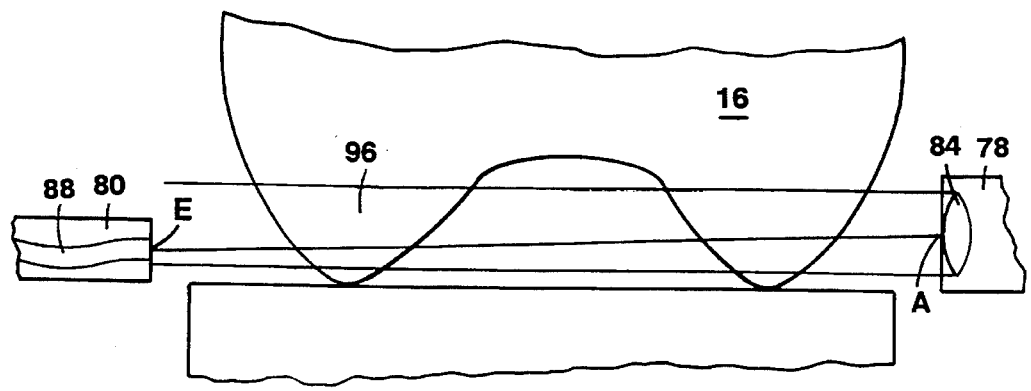
FIGS. 5 and 6 are side views of a portion of a bottle and some of the sensors of the system of FIG. 4.
Figure 5:
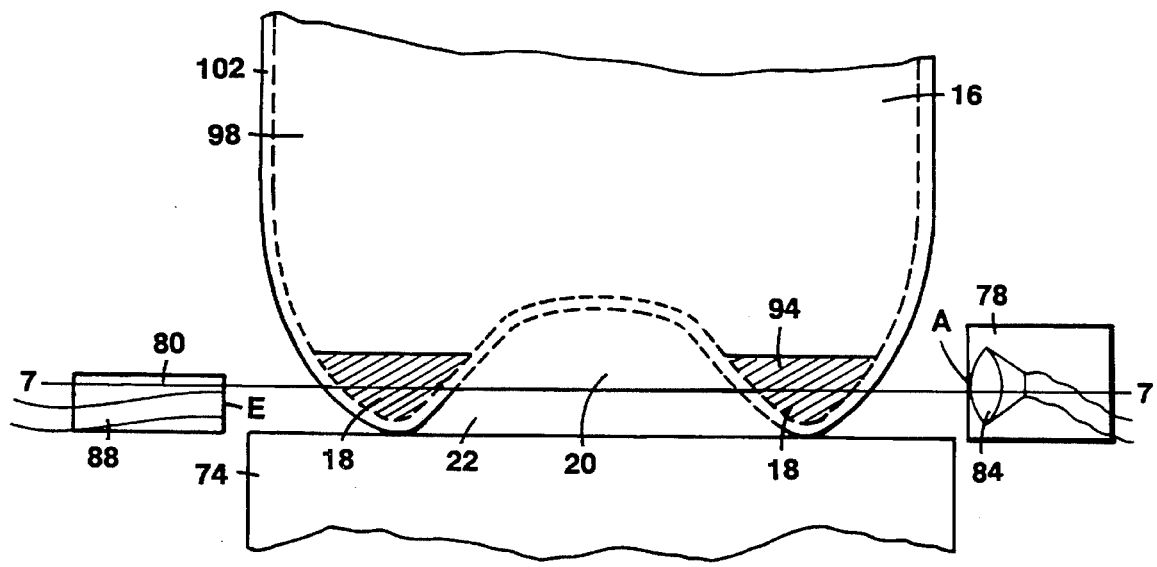

With reference to FIGS. 5 and 6, illuminator 78 and detector 80 are positioned so that the radiant energy from lens 84 is directed at a region 94 near the bottom of each bottle 16, with the lens being centered about one half inch above the bottom of the bottle, and fiber 88 being centered about one quarter inch above the bottom of the bottle. The illuminator and the detector are aimed such that their axes of emission and reception are not aligned (i.e., the illuminator and the detector, respectively, emit and receive radiation in directions that are not parallel to each other) and are not normal to the direction of movement of the bottles. This positioning requires the presence of only minimal amounts of liquid 18 in the bottle. In the preferred embodiment, each bottle needs to contain as little as about four and one half milliliters of liquid. In addition to being positioned near the bottom of the bottle, the illuminator and the detector are positioned close to the conveyor 74, typically within one eighth of an inch. As best illustrated in FIG. 6, a beam of light 96 from the illuminator is directed at and above the horizontal plane occupied by the detector. As also illustrated in FIG. 6, the mean light path from the lens of the illuminator to the fiber 88 of the detector is along path AE.

Although bottles and containers of various shapes may be inspected by system 72, the bottle 16 shown in FIGS. 1 and 5–8 has a base 22 with a convex bulge 20 in its bottom that causes liquid 18 near the bottom to form a concentric annular ring around the bulge. Because the base has a smaller diameter than a main portion 98 of the bottle, and because the illuminator and the detector are positioned near the bottom of the bottle, bottles can be moved along conveyor 74 with no spacing—i.e., in contact with other bottles, with no interference by a bottle with measurement taken by system 72 on an adjacent bottle.

As shown in FIG. 4, a liquid supplier 100, positioned upstream of illuminator 78 and radiant energy source 10, adds a sufficient amount of liquid 18 to each bottle to ensure that radiation emitted from the illuminator, and from the radiant energy source, will encounter liquid in the bottom of each bottle. Generally, because extra liquid does not affect the performance of system 72, the liquid supplier adds liquid to each bottle without regard to whether a bottle already contains liquid. Addition of liquid by the supplier 100, which may be an injector timed to inject pulses of liquid into the open top of each bottle as the bottle passes underneath the supplier, may assist in leaching contaminants from the bottle walls as well as ensuring the presence of a sufficient amount of liquid for detection. Typically, the liquid supplier delivers the liquid at high pressure, which agitates any particles resulting from turbid contaminants within the bottle and causes foam 30 to be produced if a foaming contaminant is present. When the liquid supplier delivers the liquid in multiple bursts, the first burst washes down contaminants from the wall 102 of the bottle and subsequent bursts agitate those contaminants. Typically, the liquid supplied by the liquid supplier is water or a dilute aqueous solution. However, in some applications, other liquids could be used. For example, a liquid that changes color in the presence of an otherwise difficult to detect contaminant could be used to ease detection of that contaminant.

Figure 7:
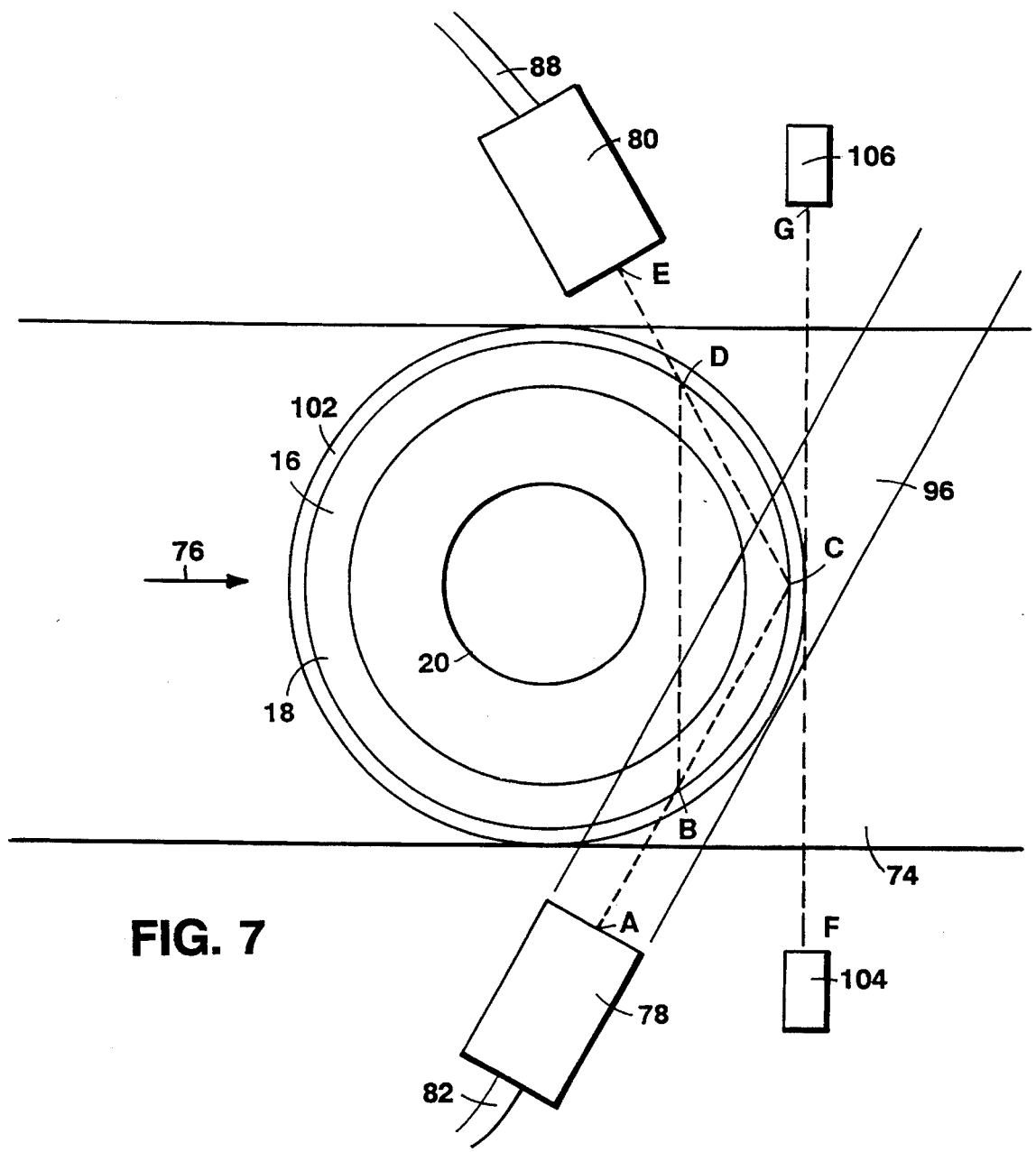
FIG. 7 is a cutaway top view taken along line 7—7 of FIG. 5 of a bottle and sensors of the system of FIG. 4 with the bottle in a first detection position.

With reference to FIG. 7, in which, for simplicity, only a single bottle 16 is shown, in operation of spectral contaminant detection system 72, a first position sensor 104 signals processor 68 when the bottle is positioned suitably to produce a first spectrum for liquid 18 and any contaminants contained therein. The first position sensor signals the processor when the bottle is positioned so that a portion of the radiant energy that reaches the detector 80 from the illuminator 78 travels along a path ABC, reflects from the inside surface of a wall 102 of the bottle, and continues along a path CDE to the detector. Because this position maximizes the length of the path that radiant energy takes through the liquid, and thereby maximizes the absorption of radiant energy by the liquid and any contaminants contained therein, the measured spectrum emphasizes absorption effects and is therefore referred to as an absorption spectrum. Typically, the illuminator and the detector are positioned so that the angle ACE is within a range from 100°–140°, with about 120° being most typical In actual operation, the portion of the radiant energy produced by the illuminator that actually reaches the detector travels by multiple paths that are significantly more complicated than the path described above. For example, the actual path is affected by reflection from the wall of the bottle and the interface between the liquid and air in the bottle. In addition, due to the presence of the liquid, the radiant energy is refracted at points B and D, so that some of it travels approximately along a path BD before reaching the detector. The radiant energy is affected also by scattering at the wall of the bottle and at the convex bulge 20, and can travel along complicated paths that include several internal reflections within the bottle.

The first position sensor 104 signals the processor 68 (FIG. 4) when the leading edge of a bottle 16 crosses a line FG between the first position sensor 104 and a first light source 106. When the bottle crosses line FG, the bottle interrupts or otherwise causes a change in the level of light (radiation) from the first light source that reaches the first position sensor. The first position sensor generates the signal to the processor 68 in response to this change in the level of light.

Upon receiving the signal from the first position sensor, the processor causes linear detection array 92 (FIG. 4) to record the spectrum produced by spectrometer 90 of the radiant energy detected by detector 80. The processor then sequentially reads the linear detection array 92 to generate a vector that represents the intensity of radiant energy received at each pixel of the linear detection array, and stores the vector as an absorption spectrum associated with the bottle being examined. The processor makes no determination as to the incident light produced by the illuminator. Typically, each pixel of the absorption spectrum is represented by twelve bits. In the preferred embodiment, the processor 68 is implemented using an Intel 486 processor running at sixty six megahertz.

Figure 8:
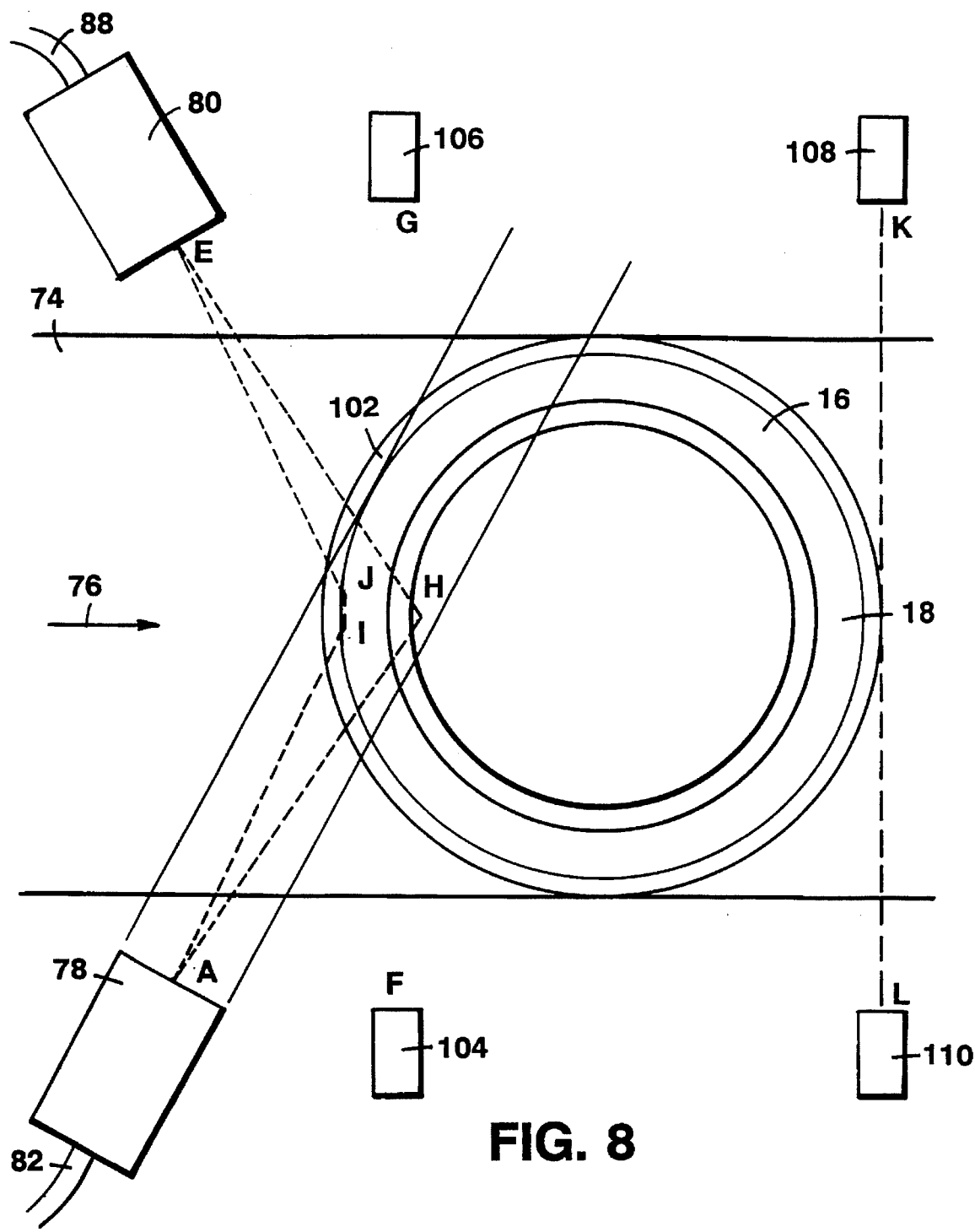
FIG. 8 is a similar view to that shown in FIG. 7, with the bottle in a second detection position.

With reference also to FIG. 8, a second position sensor 108 signals the processor when a bottle is positioned suitably to produce a second spectrum for liquid and any contaminants contained in the bottle. The second position sensor signals the processor when the bottle is positioned so that radiant energy that reaches the detector from the illuminator 78 travels approximately along a path AH, reflects from liquid 18 near the inner surface of wall 102, and continues approximately along a path HE to the detector 80. Because most of the radiant energy reaching the detector does so by reflection rather than transmission, the measured spectrum for this second position of the bottle is referred to herein as a reflection spectrum.

It should be understood that the path of the radiant energy for the measurement at a second position of the bottle is, like that of the first position, more complicated than illustrated in FIG. 8. For example, light could also travel along a path AI, refract at the interface between the wall 102 and the liquid, travel along a path IJ, refract at the interface between the liquid and the wall, and travel along path JE to the detector 108. Moreover, the intensity of the energy received by the detector for the second position is typically lower than that received for the first position since, when the bottle is in the second position, most of the energy is transmitted beyond point H.

The second position sensor 108 signals the processor 68 when a leading edge of a bottle crosses a line KL between the second position sensor and a second light source 110. The second position sensor and the second light source are typically located downstream of the first position sensor 104 and the first light source 106 by slightly less than the diameter of a bottle, and operate identically to the first position sensor and the first light source. To prevent cross talk caused by the first position sensor responding to light produced by the second light source, or by the second position sensor responding to light produced by the first light source, the sensors and light sources are positioned with the first position sensor and the second light source on one side of the conveyor 104, and the second position sensor and the first light source on the other side of the conveyor. In an alternative approach to preventing cross talk, the sensor/light source pairs are configured to respond to different frequencies of light.

Upon receiving the signal from the second position sensor, the processor 68 causes the linear detection array 92 to record the spectrum produced by the spectrometer 90 of the radiant energy detected by the detector 108. The processor then stores the recorded spectrum as a reflection spectrum associated with the bottle being examined.

Figure 9:
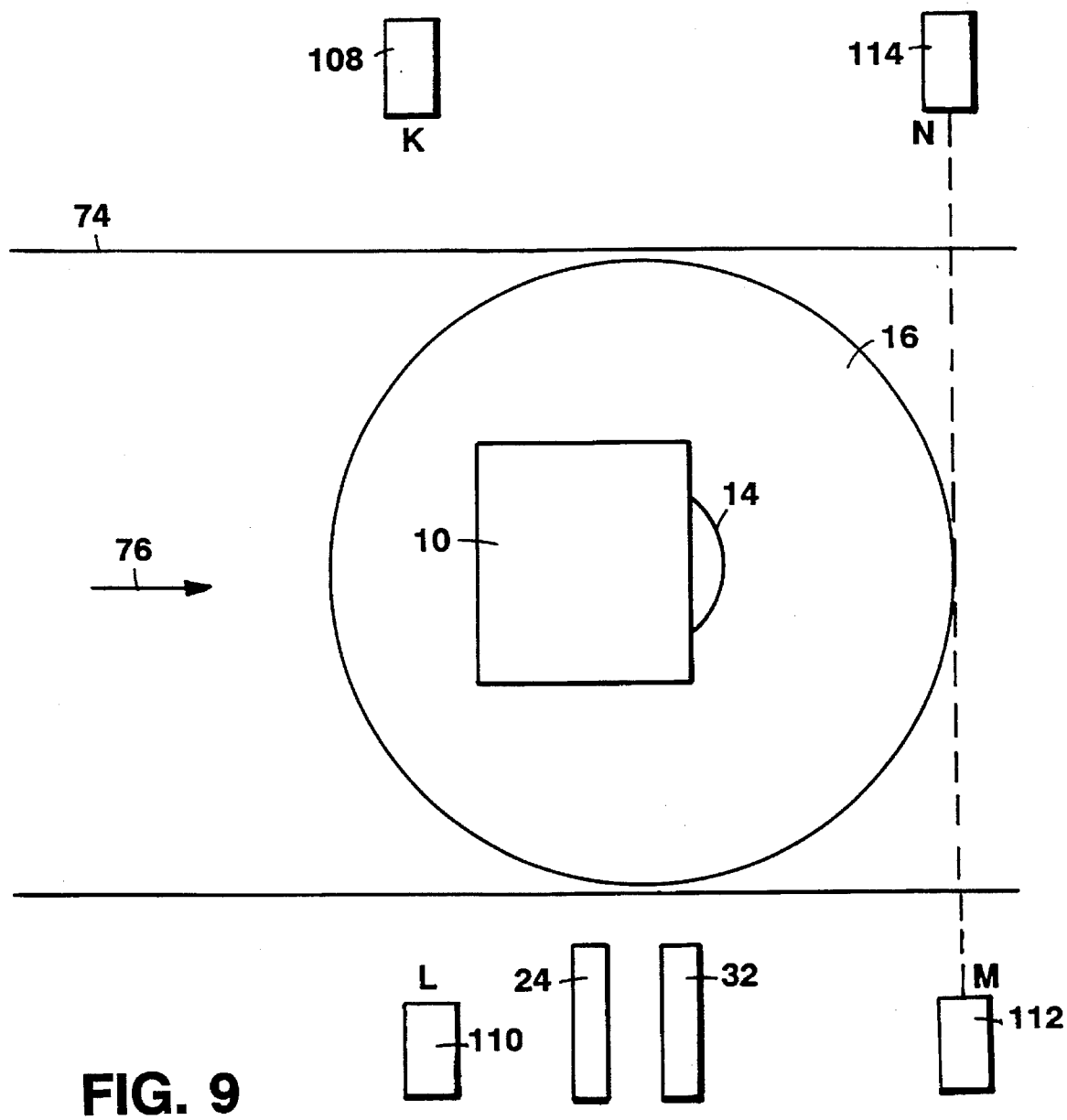
FIG. 9 is a top view of a bottle and sensors of the system of FIG. 4 with the bottle in a third detection position.

With reference also to FIG. 9, a third position sensor 112 signals the processor 68 when a bottle is positioned suitably to produce a turbidity/foam measurement for liquid and any contaminants contained in the bottle. The third position sensor signals the processor when the bottle is positioned so that scattered light from laser source 10 is directed at the turbid contaminant detector 24 and the foam detector 32, which occurs when a leading edge of a bottle crosses a line MN between the third position sensor 112 and a third light source 114. The third position sensor and the third light source are typically located downstream of the second position sensor 108 and the second light source 110, and operate identically to the second position sensor and the second light source. To prevent cross talk caused by the second position sensor responding to light produced by the third light source, or by the third position sensor responding to light produced by the second light source, the sensors and light sources are positioned with the second position sensor and the third light source on one side of the conveyor 104, and the third position sensor and the second light source on the other side of the conveyor. In an alternative approach to preventing cross talk, the sensor/light source pairs are configured to respond to different frequencies of light.

The signals from photodetectors 62, 66 and 38 are continually amplified and converted to digital values by the processor 68. Upon receiving the signal from the third position sensor, the processor latches the digital values to record the level of energy detected by photodetectors 62, 66 and 38. The processor then stores the recorded turbidity and foam energy levels for the bottle being examined.

The processor 68 utilizes spectra to determine whether a bottle 16 contains contaminants by comparing the absorption and reflection spectra associated with the bottle to a library of reference spectra associated with bottles containing acceptable substances. For example, for bottles to be filled with a beverage, acceptable substances would include water, beverage residue, and the aqueous solution supplied by liquid supplier 100. The processor compares the spectra by computing either the Pearson's correlation or the Spearman's correlation for the vectors representing each spectrum.

Pearson's correlation, which is described, for example, in Pfaffenberger & Patterson, Statistical Methods For Business and Economics, p. 429 (1977, Richard D. Irwin, Inc., Homewood, Ill.), determines whether two vectors are related by a linear mapping, and is determined as: where $x_i$ equals the ith component of the vector X minus the average value of the components of the vector X, $y_i$ equals the ith component of the vector Y minus the average value of the components of the vector Y, and n equals the number of $$r = \frac{\sum_{i=1}^{n} (x_i y_i)}{\sqrt{\sum_{i=1}^{n} (x_i)^2} \sqrt{\sum_{i=1}^{n} (y_i)^2}}$$

components in vector X or vector Y.

Spearman's correlation, which is described in Pfaffenberger & Patterson at p. 679, arranges the elements of each vector in rank order and determines whether two vectors have similar rank orders, and is determined as:

$$\rho = 1 - 6 \sum_{i=1}^{n} \frac{[R(X_i) - R(Y_i)]^2}{n(n^2 - 1)}$$

where $R(X_i)$ equals the rank of the ith component of the vector X relative to the other components of the vector X, $R(Y_i)$ equals the rank of the ith component of the vector Y relative to the other components of the vector Y, and each tied rank is assigned the average of the ranks that would have been assigned had there been no ties (e.g., if the fifth and sixth ranked components have equal values, they are each assigned a rank of 5.5).

If the spectra associated with the bottle correlate within a predefined threshold—e.g., by greater than 90%—to a pair of reference spectra representing acceptable bottle content, the processor allows the bottle to continue along the conveyor for filling or other testing. If not, the processor sends a signal to a suitable rejector 116, and the rejector responds by removing the bottle from the conveyor.

The processor also sends a signal to the rejector if the processor determines that the turbidity or foam energy levels indicate that a turbid or foaming contaminant is present in the bottle. This determination is typically varied based on the color spectra of the liquid in the bottle. For example, some carbonated beverages contain fruit juice and are slightly turbid. If the color spectra of the liquid matches reference spectra associated with such a beverage, the processor would increase the threshold at which a turbid contaminant is indicated. Similarly, if the color spectra of the liquid matches reference spectra associated with water, the processor would decrease the thresholds associated with turbidity and foaming.

An advantage of comparing the spectra associated with a bottle to reference spectra associated with bottles containing acceptable materials, rather than comparing with spectra associated with bottles containing unacceptable contaminants, is that the former imposes less computational burden on the processor. Moreover, detection accuracy of the system may be higher due to a reduced likelihood of failing to detect contaminants.

The computational burden is reduced because the number of acceptable reference spectra is typically quite limited, while, considering the number of potential contaminants and the various ways in which the contaminants can be combined, the number of unacceptable reference spectra may be virtually unlimited. For example, to detect contaminants in refillable polyethylene terephthalate cola bottles, it has been found that a library consisting of ten reference spectra—the absorption and reflection spectra associated with two liquid levels of water and three liquid levels of cola—is adequate.

The detection accuracy of the system is higher because, unlike a system in which only bottles having spectra similar to reference spectra associated with known contaminants are rejected, the system is able to reject a bottle that contains a previously unknown contaminant or a previously unknown combination of known contaminants.

Though comparison to acceptable reference spectra offers considerable advantages, the spectral contaminant detection system could be configured to compare the spectra associated with unacceptable spectra or a combination of acceptable and unacceptable spectra. For example, to screen out, for testing or other purposes, only bottles containing particular contaminants such as a blue fabric softener or a green disinfectant, the spectra associated with the bottles could be compared to reference spectra associated with the particular contaminants. Similarly, if the spectra associated with a bottle containing a particular contaminant were close to the spectra of an uncontaminated bottle, it would be useful to accept the bottle only when its spectra are sufficiently similar to the spectra of the uncontaminated bottle and sufficiently different from the spectra of the contaminated bottle.

Typically, the processor 68 combines the detection approaches as follows. If the turbid or foaming energy levels indicate the presence of turbid or foaming contaminants, the processor signals the rejector 116 to reject the bottle unless the spectral information indicates that the liquid is an acceptable turbid or foaming liquid. The processor also signals the rejector if the spectral information confirms that the liquid is unacceptable, or fails to confirm that the liquid is acceptable.

The lamp 86 of the illuminator 106 may be a wideband source that produces radiant energy in a wavelength range from about 250 nanometers to about 2000 nanometers, which includes near-ultraviolet energy, visible light and near-infrared energy. The linear detection array 92 produces spectra for the wavelength range from about 300 to 900 nanometers. Within this range, for correlation purposes, the range from about 485 to about 600 nanometers has been found to be most useful for absorption spectra, and the range from about 350 to about 750 nanometers has been found to be most useful for reflection spectra. In another approach, near-infrared or infrared wavelengths could be emphasized. This would be useful, for example, in detecting the presence of sugars in bottles to be filled with water because sugar absorbs radiation of wavelengths between 1300 and 1600 nanometers. Indeed, because infrared spectra can be used to identify almost all organic compounds, a system emphasizing the infrared spectra could be used as a general chemical detector.

Figure 10:
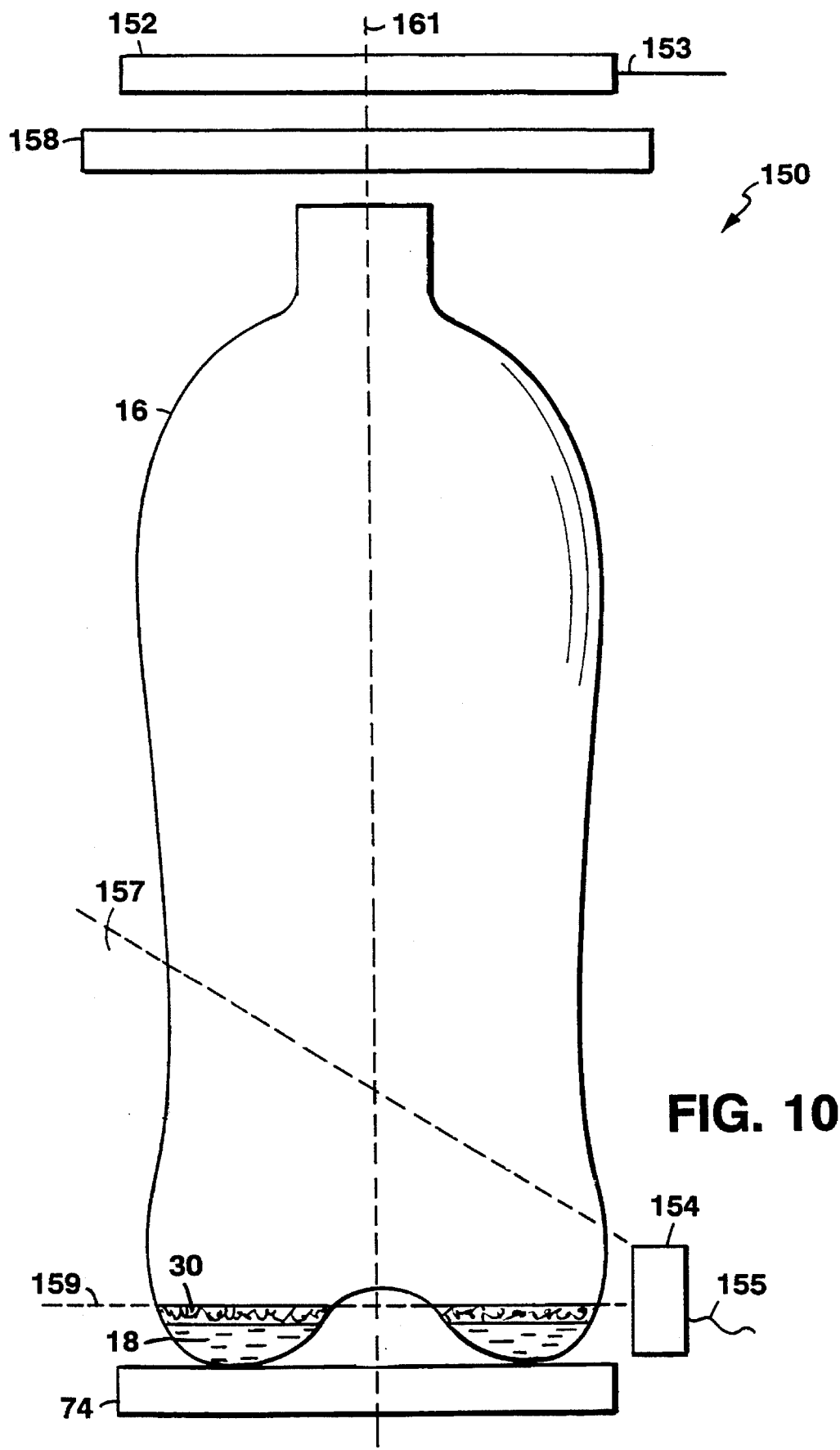
FIG. 10 is a side view of a bottle and the components of a foam detection system.
Figure 11:
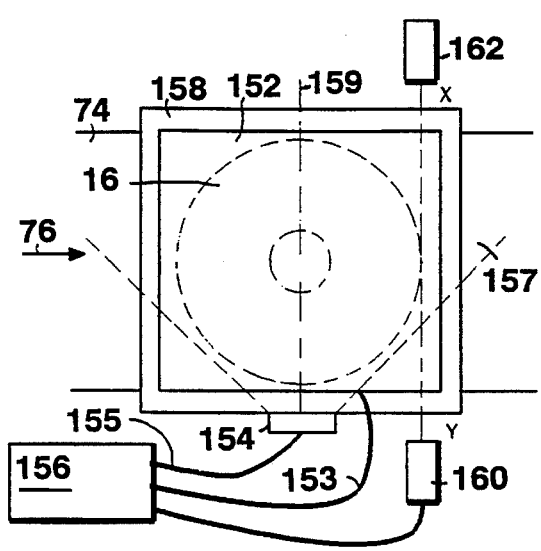
FIG. 11 is a top view of the foam detection system of FIG. 10.

With reference to FIGS. 10 and 11, in another approach, a foam detection system 150 uses digital image processing techniques to detect foaming contaminants such as detergents and soaps, particularly uncolored detergents or soaps, by detecting even low levels of foam 30 on the surface of liquid 18 in a bottle 16. Foam detection system 150 includes three basic components: an imaging device 152, an illumination source 154, and a processor 156. The imaging device 152 and the source 154 are electrically connected to the processor 156 by lines 153 and 155 respectively.

As shown, the imaging device 152 is positioned above the conveyor 74 at a height just above the height of a bottle 16 and in a plane that is parallel to the base of the bottle. Imaging device 152 is typically a high-speed, solid state device such as a CCD camera and includes an active imaging area that is slightly larger than the area of the base of a bottle 16. Imaging device 152 produces digitized signals representing the intensity of radiant energy incident on each x-y coordinate of the active imaging area. Suitable resolution has been produced using a CCD camera having a 256 by 256 array of pixels. Imaging device 152 may be implemented using a Model No. CA-D1-02518A CCD Image Sensor available from Dalsa of Waterloo, Ontario, Canada.

The illumination source 154 is positioned at the side of conveyor 74 about one centimeter above the conveyor (i.e., near the bottom of the bottle 16). In a preferred implementation, the illumination source 154 includes a square array of nine infrared light emitting diodes (LEDs) positioned beneath a molded plastic dome to produce a sixty degree cone 157 of infrared energy, with the cone having its central axis 159 parallel to the conveyor and perpendicular to the direction of travel of the bottles. The illumination source 154 is positioned relative to the imaging device 152 so that the central axis 159 of cone 157 is perpendicular to and intersects the central axis 161 of the imaging device 152. The illumination source 154 may also be implemented using a broad spectrum source, such as a xenon flashtube.

Illumination source 154 is used in combination with a wavelength-selective filter 158 that is positioned between the bottle and the imaging device. Wavelength-selective filter 158 admits the wavelength(s) of the LED or LEDs and rejects ambient light of other wavelengths. This arrangement avoids interference due to ambient lighting and also prevents the illumination source from interfering with wavelength-specific measurements in other wavelength ranges that may be deployed in close proximity, such as those used in turbid contaminant detection and/or spectral contaminant detection. Filter 158 may be implemented using a long wave pass filter that admits energy having wavelengths of 790 nanometers or greater, and blocks energy having wavelengths shorter than 790 nanometers. A suitable filter having these characteristics is the Model No. LG790 long wave pass filter available from Corion Optics of Holliston, Mass.

With reference to FIG. 11, a position sensor 160 signals processor 156 when a bottle 16 is positioned beneath imaging device 152 so as to permit imaging device 152 to produce an image of the bottle. The position sensor 160 signals the processor when the leading edge of a bottle 16 crosses a line XY between the position sensor 160 and a light source 162. When the bottle crosses line XY, the bottle interrupts or otherwise causes a change in the level of light from the light source 162 that reaches the position sensor 160. The position sensor generates the signal to the processor 156 in response to this change in the level of light.

Upon receiving the signal from position sensor 160, processor 156 activates illumination source 154 and signals imaging device 152 to latch the digitized image resulting from the activation of illumination source 154. Processor 156 then loads the latched, digitized image from imaging device 152 for further processing.

Figure 12:
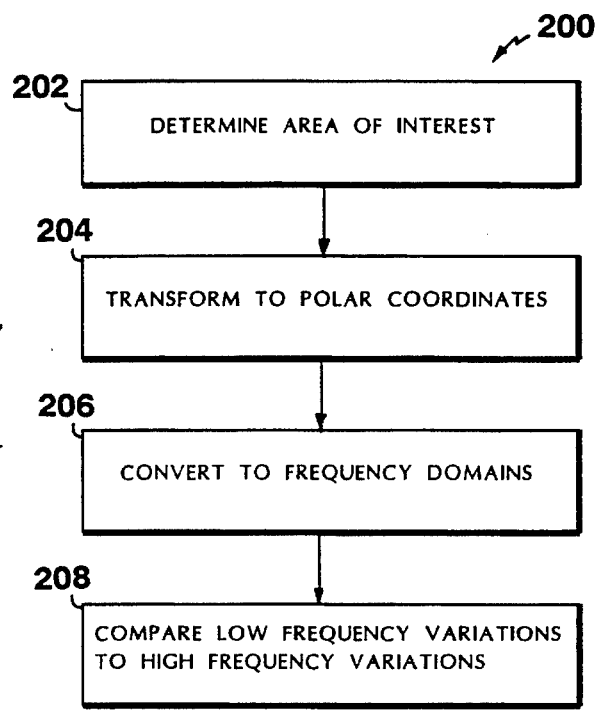
FIG. 12 is a block diagram of a procedure implemented by a processor of the foam detection system of FIG. 10.

With reference to FIG. 12, image processing is used to detect foaming contaminants according to a procedure 200. First, the area of the digitized image which is of interest for further processing is determined (step 202). Since a bottle 16 typically has a contoured circular bottom, the digitized image produced by imaging device 152 and transferred to processor 156 typically includes a set of concentric rings.

Figure 13:
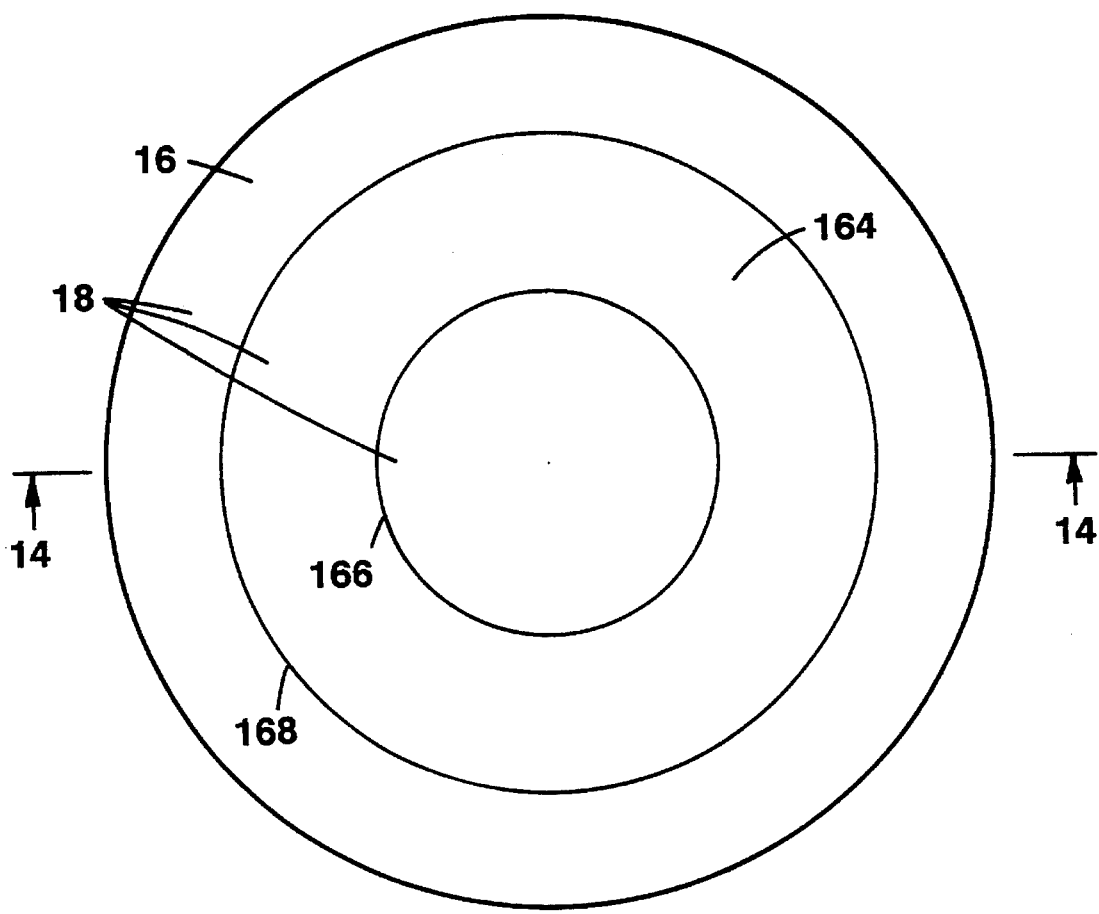
FIG. 13 is a top view of a bottle.
Figure 14:
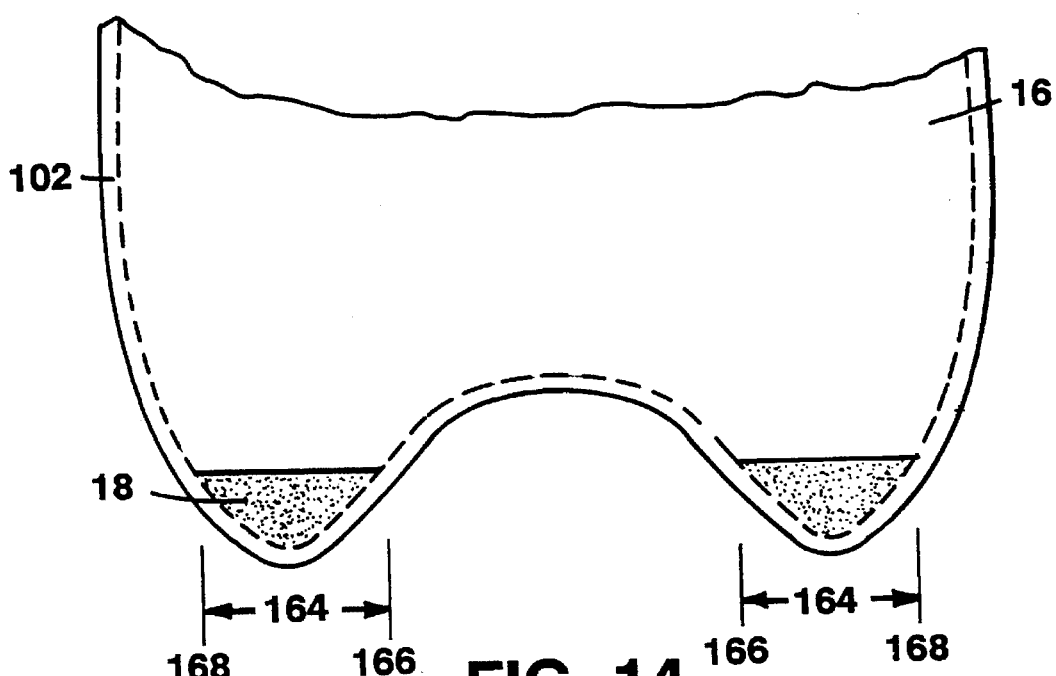
FIG. 14 is a side view taken along line 14—14 of FIG. 13 of a portion of the bottle of FIG. 13.

With reference also to FIGS. 13 and 14, for purposes of foam detection, the area of interest in the image is a ring 164 at the bottom of the bottle that contains liquid residue 18 as well as underlying bottle contours that act as unwanted and unpredictable interferences. The area of interest for foam detection is defined by a minimum radius 166 and a maximum radius 168. These radii are determined by (1) the geometry of the bottle, and (2) the minimum quantity of liquid residue in the bottle. For a given production line, both of these factors are known. (The minimum quantity of liquid is known because supplier 100 (FIGS. 4 and 15) is operated to add a known amount of liquid to each bottle 16.) Thus, the area of interest can always be defined in terms of minimum and maximum radii about the center of a bottle.

After the area of interest has been determined, processor 156 transforms the image intensity data representing the area of interest from rectangular coordinates to polar coordinates (step 204). This transformation yields a rectangular array of image intensity values as a function of angle and radius, where the entries in each row of the array represent image intensity values for different angles and a common radius, and the entries in each column of the array represent image intensity values for different radii and a common angle.

Next, processor 156 performs a two dimensional Fourier transform of the polar coordinate array to convert the intensity information to the frequency domain (step 206). The Fourier transform results in an array of complex numbers that each represent a level of spatial variation in intensity in the radial and angular dimensions. As discussed in more detail below, entries in each row of the complex array represent the distribution of angular intensity variations for a particular level of radial intensity variation. Similarly, entries in each column of the complex array represent the distribution of radial intensity variations for a particular angular intensity variation.

Processor 156 then analyzes the frequency data to determine whether a foaming contaminant is present by comparing the level of low frequency spatial variations in intensity to the level of high frequency spatial variations in intensity (step 208). A normal bottle that is dry or contains a non-foaming liquid residue will produce predominantly low frequency radial variations in intensity (caused by circular contours in the bottle) and virtually no angular variations in intensity. A bottle with a foaming residue will produce considerable high frequency radial and angular variations in intensity. Variations resulting from factors such as image misalignment, uneven lighting and stray reflections will, in general, result in low frequency spatial variations in intensity.

Processor 156 determines whether a foaming contaminant is present by determining a ratio of the level of high frequency spatial variations in intensity relative to the level of low frequency spatial variations while ignoring low frequency components that are typical of misalignment and/or uneven lighting. This ratio is then used as an index of foam residue in the bottle.

Figure 15:
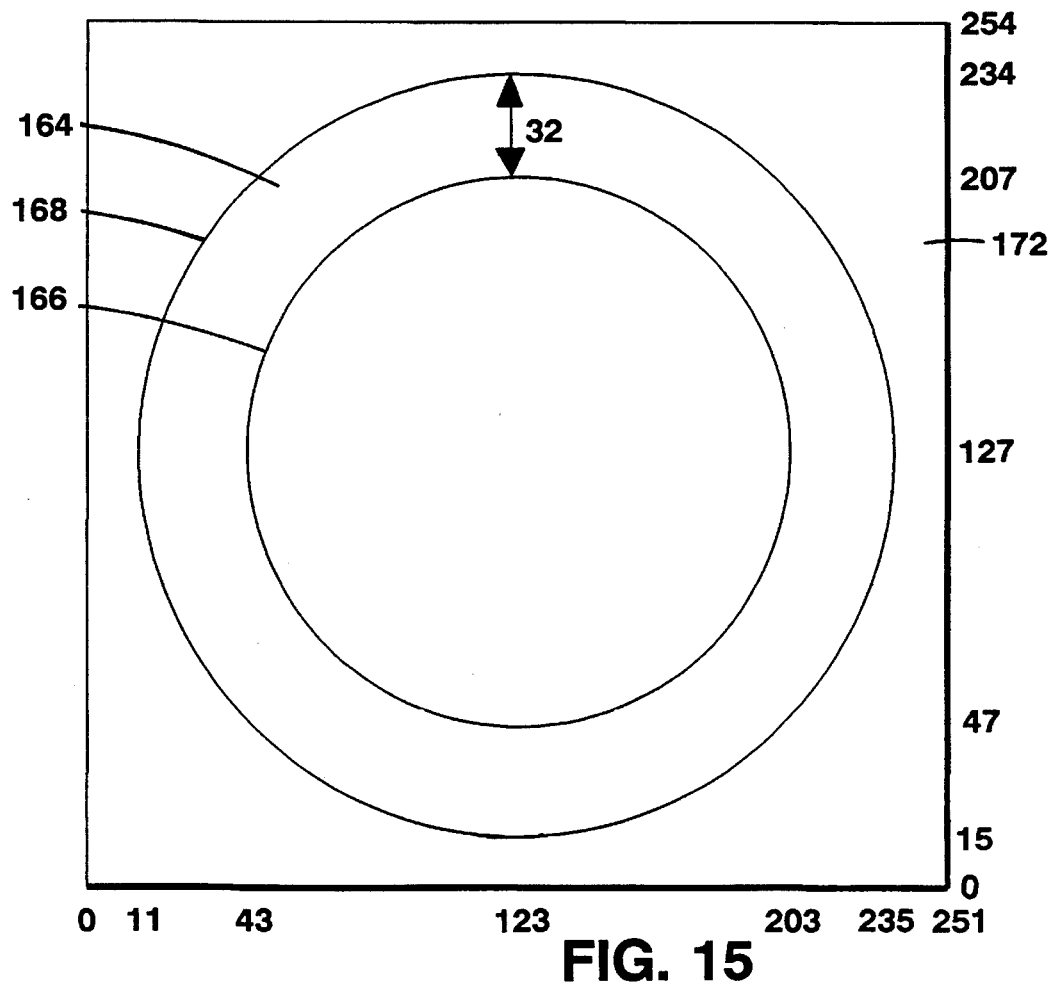
FIG. 15 is a block diagram of an image produced by a the foam detection system of FIG. 10.

With reference to FIG. 15, in a specific example of the procedure implemented by processor 156, it is assumed initially that, the imaging device 152 produces an essentially square array 172 of intensity values that includes 255 rows and 252 columns (imaging device 152 is a 256 by 256 pixel CCD that includes two columns of "dead" pixels along each vertical edge, and a single row of "dead" pixels along its top), that the minimum and maximum radii 166 and 168 for the area of interest 164 are 80 and 112, and that position sensor 160 is aligned so that when the bottle is positioned under the imaging device the x and y coordinates of the center of the bottle are 123 and 127. As noted above, misalignment of the bottle will produce low frequency variations in image intensity that will not be detected as foam, and the bottle therefore need not be perfectly aligned.

Processor 156 then converts the array of x and y coordinates for the area of interest into an array of polar coordinates having 32 rows, each of which corresponds to a particular radius, and 256 columns, each of which corresponds to a particular angle. To simplify the Fourier transform, the number of rows and the number of columns are both powers of two. The values of the entries of the polar coordinate array are determined according to:

$$\text{Polar}(i, j) = \text{Rectangle}(x_{abs}(i, j), y_{abs}(i, j))$$

where i represents the row (i.e., the radius) and j represents the column (i.e., the angle). Processor 156 determines $x_{abs}(i, j)$ as:

$$x_{abs}(i, j) = \lfloor \left( R_{min} + \frac{R_{max} - R_{min}}{Res_R} i \right) \cos\left( \frac{2\pi j}{Res_A} \right) + C_x + 0.5 \rfloor$$

where $R_{min}$ is the minimum radius of the area of interest and has a value of 80, $R_{max}$ is the maximum radius of the area of interest and has a value of 112, $Res_R$ is the radial resolution, and has a value of 32 (the number of rows in Polar(i,j)), $Res_A$ is the angular resolution and has a value of 256 (the number of columns in Polar(i,j)), and $C_x$ corresponds to the x coordinate of the center of the bottle and has a value of 123. Similarly, processor 156 determines $y_{abs}(i, j)$ as:

$$y_{abs}(i, j) = \lfloor \left( R_{min} + \frac{R_{max} - R_{min}}{Res_R} i \right) \cos\left( \frac{2\pi j}{Res_A} \right) + C_y + 0.5 \rfloor$$

where $C_y$ corresponds to the y coordinate of the center of the bottle and has a value of 127. In generating the polar coordinate array, i takes on values from 0 to $Res_R$−1 (31) and j takes on values from 0 to $Res_A$−1 (255).

Next, processor 156 performs a Fourier transform on the array of polar coordinates to produce an array having 16 rows and 128 columns, with each row in the array representing levels of angular intensity variation for a particular level of radial intensity variation, each column representing levels of radial intensity variation for a particular level of angular intensity variation, and each entry representing a combined level of radial and angular intensity variation. Thus, row zero corresponds to the angular intensity variations when there are no radial intensity variations (i.e., the pixels along each radius share a common intensity value), column zero corresponds to the radial intensity variations when there are no angular intensity variations (i.e., the pixels along each circumference share a common intensity value), and the entry that falls within both column zero and row zero corresponds to neither angular nor radial intensity variations (i.e., all pixels share a common intensity value that corresponds to the average intensity of the image). Also, the entries in the first column and the first row correspond generally to a low frequency sinusoidal artifact that is typically caused by misalignment of the bottle with the imaging device. Finally, row fifteen corresponds to the angular intensity variations when radial intensity variation is at its highest level (i.e., the pixels along each radius alternate between high and low intensity levels), column 127 corresponds to the radial intensity variations when angular intensity variation is at its highest level (i.e., the pixels along each circumference alternate between high and low intensity levels), and the entry that falls within both row fifteen and column 127 corresponds to high levels of variation in both angular and radial intensity (i.e., all neighboring pixels alternate between high and low intensity values).

Processor 156 performs the Fourier transform using the well known Fast Fourier Transform ("FFT") technique. This technique is generally described, for example, in Gonzalez & Woods, *Digital Image Processing*, pp. 81–217 (1992, Addison Wesley), and a particular software implementation of the FFT is illustrated in figure 3.23 of that text. As required by the rate of bottle throughput, the FFT and other calculations may be performed by a special purpose digital signal processing board.

After performing the Fourier transform, processor 156 determines whether a foaming contaminant is present by determining the ratio between the energy in high frequency variations and that in low frequency variations. In making this determination, processor 156 ignores the entries in row zero and column zero (which correspond to no variation in either angular or radial intensity) as well as the entries in row one and column one (which, as discussed above, correspond to low frequency artifacts introduced, for example, by misalignment of the image).

Determining energy according to a root-mean-squared approach, processor 156 determines $E_L$, the energy of low frequency variations, according to:

$$E_L = \sqrt{ \sum_{r=2}^{r=10} \left( \sum_{c=2}^{c=10} FFT(r, c)^2 \right) }$$

where r is the row, c is the column, and FFT(r, c) is an entry corresponding to row r and column c in the array resulting from the Fourier transform. As shown, the processor determines the energy of low energy variations from the entries in rows two through ten and columns two through ten. Similarly, processor 156 determines $E_H$, the energy of high frequency variations, according to:

$$E_H = \sqrt{ \sum_{r=2}^{r=15} \left( \sum_{c=11}^{c=127} FFT(r, c)^2 \right) }$$

As shown, the processor determines the high energy variations from the entries in rows two through fifteen and columns eleven through one hundred twenty seven.

After determining the high and low frequency energies, the processor divides $E_H$ by $E_L$ to determine the ratio of the energies and indicates that a foaming contaminant is present if the ratio exceeds a threshold level.

Figure 16:
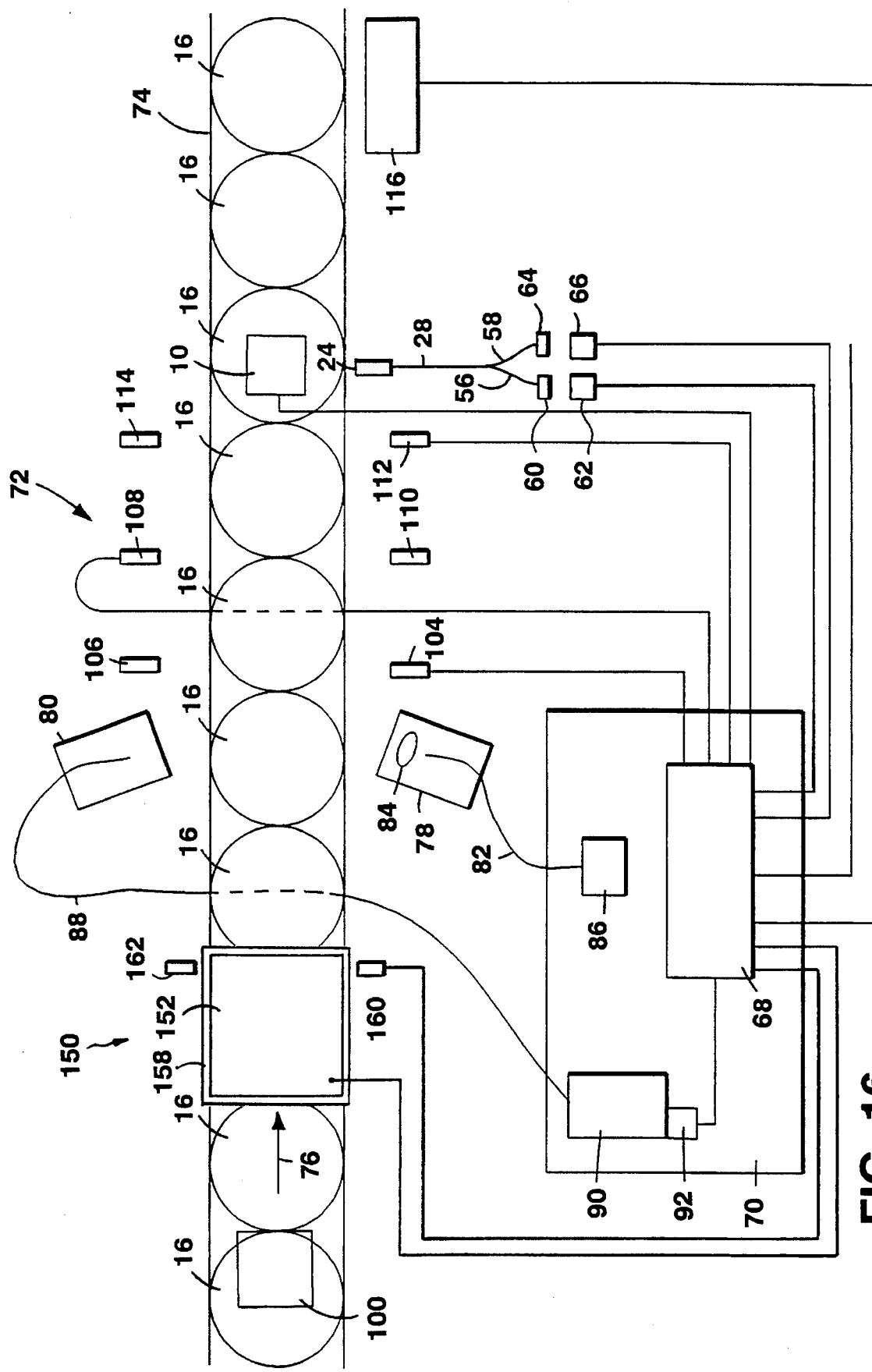
FIG. 16 is a schematic plan view of a portion of a bottle conveyor with a contaminant detection system including the foam detection system of FIG. 10.

With reference to FIG. 16, foam detection system 150 may be used in conjunction with turbid contaminant detector 24 and/or spectral contaminant detection system 72. In this case, foam detection system 150 may, for example, replace foam detector 32 (see FIGS. 1 and 4) with the functions of processor 156 being implemented by processor 68.

The combination of foam detection system 150 with spectral contaminant detection system 72 and/or turbid contaminant detector 24 offers considerable advantages. For example, dilute detergent residues and flavored beverage residues such as those resulting from cola-flavored beverages may display similar bubble patterns so as to be indistinguishable based on foam detection alone. In this case, the foam measurement could be correlated with other optical measurements, such as those produced by spectral contaminant detection system 72, to distinguish between the beverage residues and the very dilute detergent residues.

Liquid supplier 100 emits jets of fluid that vigorously disrupt the surface of the liquid in the bottles 16. In some instances, this vigorous disruption enables the system to distinguish between the foaming produced by dilute detergent residues that occur when a bottle containing detergent is rinsed with water prior to being returned by a consumer and air bubbles that may be produced in non-foaming liquids such as water or beverage residue in the bottom of a bottle. Because the foaming produced by vigorous disruption will be more intense and will persist much longer for foaming liquids, even when substantially diluted, than for non-foaming liquids, use of such disruption enables system 150 to identify dilute foaming liquids. Other approaches to producing suitable foam include mechanically striking the bottles or using the motion of the conveyor to cause bottles to impact against a stationary structure, such as a flexible vane or strut that protrudes into the path of the bottles.

The invention may be in the form of other embodiments. For example, though conveyor 104 is illustrated as a straight conveyor, the system could be applied effectively to a system in which the bottles are held in the periphery of a rotating wheel as they pass by the illuminator 106 and the detector 108. In this case, though bottles would travel in an arc as they moved from the first position to the second position, their spectra would still be determined as illustrated in FIGS. 7 and 8. In another variation, the contaminant detection system may generate and utilize only a single spectrum, such as an absorption spectrum or a reflection spectrum, for each bottle. Limited tests with a system utilizing an absorption spectrum alone or a reflection spectrum alone have generally shown lower overall accuracy in detection of contaminants, and have tended to produce more false positives than a system generating and using both absorption and reflection spectra. However, a single spectrum may be adequate in certain applications. For example, an absorption spectrum may be sufficient for detection of contaminants in liquid/contaminant mixtures of high transmissivity.

Also, instead of varying the position of the bottle relative to the illuminator and the detector to obtain different spectral characteristics, two or more sets of illuminators and detectors, having similar or different characteristics, and being operable simultaneously or sequentially, could be employed. For example, a first illuminator and detector pair could be configured and oriented to obtain a visible absorption spectrum while a second illuminator and detector pair was configured to obtain an infrared reflection spectrum.

In addition, detection of turbid contaminants could be combined with spectral detection using only a single detector. In this approach, the spectral energy source 10 would be positioned so that light scattered by turbid contaminants would strike the detector 80. The processor would then determine that a turbid contaminant was present whenever the spectrum of the liquid took on an excessive value at the one or more wavelengths produced by the laser source.

Finally, transmitted light could be measured rather than scattered light in the detection of turbid contaminants. In this approach, the turbid contaminant detector would be placed under the bottle, and the presence of a turbid contaminant would be signalled when the level of energy received by the detector is less than a particular threshold.

What is claimed is:

1. A method of detecting a turbid contaminant in a moving container, comprising:

selecting a wavelength for which energy having said wavelength is absorbed by contents of the moving container that include the turbid contaminant at a different level than energy having said wavelength is absorbed by contents of the moving container that include a non-contaminant, producing radiant energy having said wavelength, directing the radiant energy into the moving container, electronically detecting a level of radiant energy scattered by contents of the moving container, and indicating the presence of a turbid contaminant when the detected level of scattered radiant energy differs from a threshold level.

2. The method of claim 1, wherein, when the moving container is a refillable plastic bottle initially filled with a liquid and the contents of the bottle may include residue of the liquid, said selecting step comprises selecting the wavelength so that energy having the wavelength is strongly absorbed by the liquid residue.

3. The method of claim 1, wherein said selecting step comprises selecting said wavelength so that energy having said wavelength is absorbed by the contents of the moving container that include the non-contaminant to a greater degree than energy having said wavelength is absorbed by contents of the moving container that include the turbid contaminant.

4. The method of claim 3, wherein said detecting step comprises detecting a level of radiant energy having said wavelength and scattered by the contents of the moving container, and wherein said indicating step comprises indicating the presence of a turbid contaminant when the detected level of scattered radiant energy exceeds the threshold level.

5. The method of claim 4, wherein said directing step comprises directing the radiant energy in a first direction and said detecting step comprises measuring a level of radiant energy having the selected wavelength that is scattered in a second direction that is different from the first direction.

6. The method of claim 5, wherein the directing step comprises directing radiant energy into an open top of the moving container, and wherein the detecting step comprises electronically detecting a level of radiant energy scattered through a side of the moving container near a bottom of the moving container by contents of the moving container.

7. The method of claim 1 further comprising adding a quantity of liquid to the moving container prior to said directing step, and wherein said directing step includes directing radiant energy at the moving container near the bottom thereof.

8. The method of claim 7, wherein said directing step comprises directing radiant energy into an opening in the moving container.

9. The method of claim 1, wherein said wavelength is a first wavelength and said producing step further comprises producing radiant energy having one or more wavelengths that differ from the first wavelength.

10. The method of claim 9, wherein the radiant energy includes radiant energy having a second wavelength, and wherein:

said detecting step comprises electronically detecting a level of radiant energy scattered by contents of the moving container and having the second wavelength, and said indicating step comprises indicating the presence of a turbid contaminant when the detected level of scattered radiant energy having the second wavelength differs from the threshold level.

11. The method of claim 10, wherein said directing step comprises directing the radiant energy in a first direction and said detecting step comprises measuring a level of radiant energy having the second wavelength that is scattered in a second direction that is different from the first direction.

12. The method of claim 10, wherein said directing step includes:

forming a first laser beam including radiant energy of the first wavelength, forming a second laser beam including radiant energy of the second wavelength, combining the first and second laser beams to form a third beam, and directing the third beam into the moving container.

13. The method of claim 10, wherein said detecting steps comprise:

detecting radiant energy scattered by the contents of the moving container, dividing the detected radiant energy into a first portion and a second portion, detecting the first level of scattered radiant energy from the first portion of detected radiant energy, and detecting from the second portion of detected radiant energy a second level of radiant energy scattered by contents of the moving container and having the first wavelength.

14. The method of claim 10, wherein the level of scattered radiant energy having the second wavelength comprises a first level of scattered radiant energy, and wherein:

said detecting step comprises detecting a second level of radiant energy scattered by contents of the moving container and having the first wavelength, and said indicating step comprises, when the first level of scattered radiant energy differs from the threshold level, comparing the first and second levels of scattered radiant energy and indicating the presence of a turbid contaminant when the first and second levels of scattered radiant energy differ in a way that indicates that a turbid contaminant is present.

15. The method of claim 14, wherein said selecting step comprises selecting the first and second wavelengths so that energy having the first wavelength is absorbed by contents of the moving container that include the non-contaminant to a greater extent than is energy having the second wavelength, and wherein said indicating step comprises indicating the presence of a turbid contaminant when the first level of scattered radiant energy exceeds the threshold level and the first and second levels of scattered radiant energy, when compared, satisfy a predetermined criterion.

16. The method of claim 15, wherein comparing the first and second levels of scattered radiant energy comprises producing a ratio of the second level of scattered radiant energy to the first level of scattered radiant energy, and wherein said indicating step comprises indicating the presence of a turbid contaminant when the first level of scattered radiant energy exceeds the threshold level and the ratio exceeds a predetermined value.

17. A turbid contaminant detection system comprising:

a radiant energy source for producing radiant energy having a wavelength that is absorbed by contents of a moving container that include the turbid contaminant at a different level than energy having said wavelength is absorbed by contents of the moving container that include a non-contaminant, the radiant energy source being positioned to direct the radiant energy into the moving container, a detector for detecting a level of radiant energy scattered by contents of the moving container, and a processor for indicating the presence of a turbid contaminant when the detected level of scattered radiant energy differs from a threshold level.

18. The system of claim 17, wherein the processor is an electronic computer operable to process information from at least 400 containers per minute.

19. The system of claim 17, wherein the detector is positioned outside of, and near the bottom of, the moving container and is operable to detect light scattered by turbid liquid within the moving container.

20. The system of claim 17, wherein the radiant energy source is operable to produce energy having a wavelength that is absorbed by contents of the moving container that include the non-contaminant to a greater extent than energy having said wavelength is absorbed by contents of a moving container that include the turbid contaminant.

21. The system of claim 20, wherein the detector is operable to detect a level of radiant energy having the wavelength and scattered by the contents of the moving container, and wherein the processor is operable to indicate the presence of a turbid contaminant when the detected level of scattered radiant energy exceeds the threshold level.

22. The system of claim 21, wherein the radiant energy source is positioned to direct the radiant energy in a first direction and the detector is positioned to measure a level of radiant energy having the selected wavelength that is scattered in a second direction that is different from the first direction.

23. The system of claim 22, wherein the radiant energy source is positioned to direct radiant energy into an open top of the moving container, and wherein the detector is positioned to measure a level of radiant energy scattered through a side of the moving container near a bottom of the moving container by contents of the moving container.

24. The system of claim 17, wherein the radiant energy source is operable to produce radiant energy having multiple wavelengths.

25. The system of claim 24, wherein:

the radiant energy source is operable to produce (a) radiant energy having a first wavelength that is absorbed by contents of the moving container that include the turbid contaminant at a different level than energy having the first wavelength is absorbed by contents of the moving container that include the non-contaminant and (b) radiant energy having a second wavelength, the detector is operable to detect a level of radiant energy scattered by contents of the moving container and having the second wavelength, and the processor is operable to indicate the presence of a turbid contaminant when the detected level of scattered radiant energy having the second wavelength differs from the threshold level.

26. The system of claim 25, wherein the level of scattered radiant energy having the second wavelength comprises a first level of scattered radiant energy, and wherein:

the detector is operable to detect a second level of radiant energy scattered by contents of the moving container and having the first wavelength, and the processor is operable to compare the first and second levels of scattered radiant energy when the first level of scattered radiant energy differs from the threshold level and to indicate the presence of a turbid contaminant when the first level of scattered radiant energy differs from the threshold level and the first and second levels of scattered radiant differ in a way that indicates that a turbid contaminant is present.

27. The system of claim 26, wherein energy having the first wavelength is absorbed by contents of the moving container that include the non-contaminant to a greater extent than energy having the second wavelength, and wherein the processor is operable to indicate the presence of a turbid contaminant when the first level of scattered radiant energy exceeds the threshold level and the first and second levels of scattered radiant energy, when compared, satisfy a predetermined criterion.

28. The system of claim 27, wherein the processor is operable to produce a ratio of the second level of scattered radiant energy to the first level of scattered radiant energy, and to indicate the presence of a turbid contaminant when the first level of scattered radiant energy exceeds the threshold level and the ratio exceeds a predetermined value.

29. The system of claim 25, wherein the radiant energy source is positioned to direct the radiant energy in a first direction and the detector is positioned to measure a level of radiant energy that is scattered in a second direction that is different from the first direction.

30. The system of claim 25, wherein the radiant energy source comprises:

a first laser source for producing a first laser beam having energy of the first wavelength and a second laser source for producing a second laser beam having energy of the second wavelength.

31. The system of claim 30, wherein the radiant energy source further comprises a dichroic reflector for combining the first and second laser beams to produce a third beam.

32. The system of claim 31, wherein the radiant energy source further comprises an adjustable positioning mirror for directing the third beam into the moving container.

33. For use with a moving container inspection system having a conveyor for moving containers and a liquid supplier for adding uncontaminated liquid to each container, a turbid contaminant detector to be mounted near said conveyor at a location downstream of the liquid supplier, said turbid contaminant detector comprising:

a radiant energy source for producing radiant energy having a wavelength that is absorbed by contents of the moving container that include a turbid contaminant at a different level than energy having the wavelength is absorbed by contents of the moving container that include a non-contaminant, the radiant energy source being positioned to direct the radiant energy into a moving container, a detector for detecting a level of radiant energy scattered by contents of the moving container, and a processor for monitoring the detected level of radiant energy and indicating the presence of a turbid contaminant when the detected level of scattered radiant energy differs from a threshold level.

* * * * *